United States Patent
Simpson et al.

(10) Patent No.: US 6,236,945 B1
(45) Date of Patent: May 22, 2001

(54) APPARATUS AND METHOD FOR THE GENERATION, SEPARATION, DETECTION, AND RECOGNITION OF BIOPOLYMER FRAGMENTS

(75) Inventors: John W. Simpson, Branford; Jonathan Marc Rothberg, Guilford; Gregory T. Went, Madison, all of CT (US)

(73) Assignee: CuraGen Corporation, New Haven, CT (US)

( * ) Notice: Subject to any disclaimer, the term of this patent is extended or adjusted under 35 U.S.C. 154(b) by 0 days.

(21) Appl. No.: 09/300,703

(22) Filed: Apr. 26, 1999

Related U.S. Application Data

(62) Division of application No. 08/438,231, filed on May 9, 1995, now Pat. No. 6,017,434.

(51) Int. Cl.[7] .............................. G01N 33/48; C12Q 1/68; C12P 19/34; C07H 21/04
(52) U.S. Cl. ................................ 702/20; 435/6; 435/91.1; 436/94; 436/800; 536/23.1; 536/24.3; 536/24.33
(58) Field of Search .............................. 435/6, 91.1, 91.2, 435/183, 194, 287.2; 436/94, 800; 536/23.1, 24.3, 24.33, 25.3; 702/20

(56) References Cited

U.S. PATENT DOCUMENTS

| | | |
|---|---|---|
| 3,603,688 | 9/1971 | DeBitetto ............................. 356/172 |
| 3,677,930 | 7/1972 | Meshbane et al. ................... 204/299 |
| 4,351,611 | 9/1982 | Leif ...................................... 356/328 |
| 4,624,768 | 11/1986 | Yoshida ........................... 204/299 R |
| 4,675,095 | 6/1987 | Kambara et al. .................... 204/299 |
| 4,811,218 | 3/1989 | Hunkapiller et al. ........... 364/413.01 |
| 4,832,815 | 5/1989 | Kambara et al. .................... 204/299 |
| 4,874,492 | 10/1989 | Mackay ............................. 204/182.8 |
| 4,908,112 | 3/1990 | Pace .................................... 204/299 |
| 5,011,284 | 4/1991 | Tedesco et al. ...................... 356/301 |
| 5,066,382 | 11/1991 | Weinberger et al. .. |
| 5,069,769 | 12/1991 | Fujimiya et al. ................. 204/182.8 |
| 5,124,247 | 6/1992 | Ansorge .................................... 435/6 |
| 5,126,022 | 6/1992 | Soane et al. .......................... 204/180 |

(List continued on next page.)

FOREIGN PATENT DOCUMENTS 0 376 611 A2    12/1989    (EP) .

OTHER PUBLICATIONS

Ahn et al., 1993, "A fully integrated micromachined magnetic particle manipulator and separator", *J. Micromechanical Syst.* 2(1):15–22.

(List continued on next page.)

*Primary Examiner*—Bradley L. Sisson
(74) *Attorney, Agent, or Firm*—Pennie & Edmonds LLP

(57) ABSTRACT

This invention is an integrated instrument for the high-capacity electrophoretic analysis of biopolymer samples. It comprises a specialized high-voltage, electrophoretic module in which the migration lanes are formed between a bottom plate and a plurality of etched grooves in a top plate, the module permitting concurrent separation of 80 or more separate samples. In thermal contact with the bottom plate is a thermal control module incorporating a plurality of Peltier heat transfer devices for the control of temperature and gradients in the electrophoretic medium. Fragments are detected by a transmission imaging spectrograph which simultaneously spatially focuses and spectrally resolves the detection region of all the migration lanes. The spectrograph comprises a transmission dispersion element and a CCD array to detect signals. Signal analysis comprises the steps of noise filtering, comparison in a configuration space with signal prototypes, and selection of the best prototype. Optionally post-processing is done by a Monte-Carlo simulated annealing algorithm to improve results. Optionally, an array of micro-reactors can be integrated into the instrument for the generation of sequencing reaction fragments directly from crude DNA samples.

15 Claims, 19 Drawing Sheets

U.S. PATENT DOCUMENTS

| | | | |
|---|---|---|---|
| 5,135,627 | 8/1992 | Soane | 204/182.8 |
| 5,137,613 | 8/1992 | Brumley, Jr. et al. | 204/299 |
| 5,141,609 | 8/1992 | Sweedler | 204/180.1 |
| 5,149,416 | 9/1992 | Osterhoudt et al. | |
| 5,162,654 | 11/1992 | Kostichka et al. | 250/458.1 |
| 5,171,534 | 12/1992 | Smith et al. | 422/82.05 |
| 5,192,412 | 3/1993 | Kambara et al. | 204/299 R |
| 5,192,450 | 3/1993 | Heyman | 210/748 |
| 5,207,886 | 5/1993 | Lauer et al. | 204/299 |
| 5,216,484 | 6/1993 | Chao et al. | 356/326 |
| 5,221,518 | 6/1993 | Mills | 422/62 |
| 5,228,971 | 7/1993 | Brumley, Jr. et al. | 204/299 |
| 5,242,568 | 9/1993 | Ehr et al. | 204/299 |
| 5,246,886 | 9/1993 | Nasu et al. | 437/228 |
| 5,253,329 | 10/1993 | Villarreal et al. | 395/24 |
| 5,268,080 | 12/1993 | Kambara et al. | 204/182.8 |
| 5,290,419 | 3/1994 | Kambara et al. | 204/299 |
| 5,304,488 | 4/1994 | Cohen et al. | 435/291 |
| 5,362,957 | 11/1994 | Nakai et al. | 250/208.1 |
| 5,366,608 | 11/1994 | Kambara | 204/299 R |
| 5,427,663 | 6/1995 | Austin et al. | 204/180.1 |
| 5,436,129 | 7/1995 | Stapleton | 435/6 |
| 5,534,703 | 7/1996 | Kambara et al. | 250/458.1 |
| 5,652,681 | 7/1997 | Chen et al. | 359/831 |

OTHER PUBLICATIONS

Aldroubi and Garner, 1992, "Minimal electrophoresis time for DNA sequencing", *BioTechniques* 13(4):620–624.

Anon, 1995, "DNA diagnostic tools for the 21st Century", *Nature Medicine* 1(2):102.

Baba et al., Jun. 1992, "Preparation of polyacrylamide gel filled capillaries for ultrahigh resolution of polynucleotides by capillary gel electrophoresis", *Anal. Chem.* 64:1221–1225.

Balch et al., 1994, "Sequencing of DNA by gel electrophoresis in micromachined channels", *Genome Science and Technology*, Abstract C–2, Venter (ed.), Conference VI, Sep. 17–21, 1994, Mary Ann Liebert, Inc. (publisher).

Ball et al., 1992, "The use of uracil–N–glycosylase in the preparation of PCR products for direct sequencing", *Nucleic Acids Res.* 20(12):3255.

Bonfield et al., 1995, "The application of numerical estimates of base calling accuracy to DNA sequencing projects", *Nucleic Acid Res.* 23(8):1406–1410.

Brewer et al., 1994, "Three dimensional imaging of DNA fragments during electrophoresis using a confocal detector", *Genome Science and Technology*, Abstract C–3, Venter (ed.), Conference VI, Sep. 17–21, 1994, Mary ann Liebert, Inc. (publisher).

Brumley, Jr. and Smith, 1994, "Rapid DNA sequencing by horizontal ultrathin gel electrophoresis", *Nucleic Acids Res.* 19(15):4121–4126.

Cantor et al., 1992, "Report on the sequencing by hybridization workshop", *Genomics* 13:1378–1382.

Chang amd Lippmann, 1993, "A boundary hunting radial basis function classifier which allocates centers constructively", Advances in neural information processing systems 5, Hanson et al. (eds.) Morgan Kaufmann.

Chen et al., 1994, "Laser desorption mass spectrometry for fast DNA analysis and sequencing", *Genome Science and Technology*, Abstract C–4, Venter (ed.), Conference VI, Sep. 17–21, 1994, Mary Ann Liebert, Inc. (publisher).

Chen, 1992, "Two–label peak–height encoded DNA sequencing by capillary gel electrophoresis: three examples", *Nucleic Acids Res.* 20(18):4873–4880.

Crompton and Brownlee, 1988, "Capillary electrophoresis", *BioTechniques* 6(5):432–439.

Drmanac et al., Jun. 1993, "DNA sequence determination by hybridization: A strategy for efficient large–scale sequencing", *Science* 260:1649–1652.

Effenhauser et al., 1994, "High–speed separation of antisense oligonucleotides on a micromachined capillary electorphoresis device", *Anal. Chem.* 66:2949–2953.

Effenhauser et al., Oct. 1993, "Glass chips for high–speed capillary electrophoresis separations with submicrometer plate heights", *Anal. Chem.* 65:2637–2642.

Efremow et al., Jan./Feb. 1986, "Anisotropic etching of Al by a directed $CI_2$ flux", *J. Vac. Sci. Technol B* 4(1):337–340.

Froussard, 1992, "A random–PCR method (rPCR) to construct whole cDNA library from low amounts of RNA", *Nucleic Acids Res.* 20(11):2900.

Frolinghaus et al., 1994, "Hierarchical neural networks for time–series analysis and control", *Comp. in Neural Syst.* 5:1–16.

Giddings et al., 1993, "An adaptive, object oriented strategy for base calling in DNA sequence analysis", *Nucleic Acids Res* 21(19):4530–4540.

Golden et al., 1993, "Pattern recognition for automated DNA sequencing: I. On–line signal conditioning and feature extraction for base calling", Proc. of First Int'l. Conf. on Intelligent System for Molecular Biology, Hunter et al. (eds.), AAAI Press, Menlo Park, CA.

Harrison et al., Sep. 1992, "Capillary electrophoresis and sample injection systems integrated on a planar glass chip", *Anal. Chem.* 64:1926–1932.

Harrison et al., Aug. 1993, "Micromachining a miniaturized capillary electrophoresis–based chemical analysis system on a chip", *Science* 261:895–897.

Hertz et al., 1991, "Introduction to the Theory of Neural Computation, Santa Fe Institute, Studies in the Sciences of Complexity", Addison–Wesley, vol. 1:217–251.

Huang et al., Sep. 1992, "DNA sequencing using capillary array electrophoresis", *Anal. Chem.* 64:2149–2154.

Huber et al., 1993, "High–resolution liquid chromatography of DNA fragments of non–porous poly(strene–divinylbenzene) particles" *Nucleic Acids Res.* 21(5):1061–1066.

Hultman et al., 1989, "Direct solid phase sequencing of genomic and plasmid DNA using magnetic beads as solid support", *Nucleic Acids Res.* 17(3):4937–4946.

Jacobson et al., Apr. 1994, "Effects of injection schemes and column geometry on the performance of microchip electrophoresis devices", *Anal. Chem.* 66(7):1107–1113.

Jacobson and Arlinghaus, Mar. 1992, "Development of resonance ionization spectroscopy for DNA sequencing and genome mapping" *Anal. Chem.* 64(5):315–328.

Jerman, 1991, "Electrically–activated, normally–closed diaphragm valves", Int'l. Conf. on Solid State Sensors, San Francisco, CA, Jun. 24–28, 1991.

Ju et al., 1996, "Energy transfer primers: A new fluorescence labeling paradigm for DNA sequencing and analysis", *Nature Medicine* 2(2):246–249.

Ju et al., 1995, "Fluorescence energy transfer dye–labeled primers for DNA sequencing and analysis", *Proc. Natl. Acad. Sci. USA* 92:4347–4351.

Karger et al., 1991, "Multiwavelength fluorescence detection for DNA sequencing using capillary electrophoresis", *Nucleic Acids Res.* 19(18):4955–4962.

Kostichka et al., Jan. 1992, "High speed automated DNA sequencing in ultrathin slab gels", *BioTechnology* 10:78–81.

Koutny and Yeung., Jan. 1993, "Expert system for data acquisition to achieve a constant signal–to–noise ratio: Application to imaging of DNA sequencing gels", *Anal. Chem.* 65:148–152.

Koutny and Yeung, Jan. 1993, "On–line detection of proteins in gel electrophoresis by ultraviolet absorption and by native fluorescence utilizing a charge–coupled device imaging system", *Anal. Chem.* 65:183–187.

Kuhr and Monnig, Jun. 1992, "Capillary Electrophoresis", *Anal. Chem.* 64:389R–407R.

Lagerkvist et al., Mar. 1994, "Manifold sequencing: Efficient processing of large sets of sequencing reactions", *Proc. Natl. Acad. Sci. USA* 91:2245–2249.

Liang and Pardee, Aug. 1992, "Differential display of eukaryotic messenger RNA by means of the polymerase chain reaction", *Science* 257:967–971.

Liang et al., 1993, "Distribution and cloning of eukaryotic mRNAs by means of differential display: refinements and optimization", *Nucleic Acids Res.* 21(14):3269–3275.

Lin et al., 1991, "Microbubble powered actuator", International Conference on Solid State Sensors, and Actuators, Transducers, San Francisco, CA Jun. 1991 pp. 1041–1044.

Loewen et al., Oct. 1977, "Grating efficiency theory as it applies to blazed and holographic gratings", *Applied Optics* 16(10):2711–2721.

Lutze et al., Jan. 1989, "Anisotropic reactive ion etching of aluminum using $CI_2$, $BCI_3$, and $CH_4$ gases", *J. Electrochem. Soc.* 137:249–252.

Mardis et al., 1995, "Resistance heating device reduces gas mobility compressions in automated fluorescent sequencing", *BioTechniques* 18:622–624.

Mathies and Stryer, 1986, "Single–molecule fluorescence detection: A feasibility study using phycoerythrin", *Applications of Fluorescence in the Biomedical Sciences* 129–140.

Mathies and Huang, Sep. 1992, "Capillary array electrophoresis: an approach to high–speed, high–throughput DNA sequencing", *Nature* 359:167–169.

Middendorf et al., 1992, "Continuous, on–line DNA sequencing using a versatile infrared laser scanner/electrophoresis apparatus", *Electrophoresis* 13:487–494.

Milofsky and Yeung, Jan. 1993. "Native fluorescence detection of nucleic acids and DNA restriction fragments in capillary electrophoresis", Anal. Chem. 65:153–157.

Nelson et al., Mar. 1993, "Sequencing two DNA templates in five channels by digital compression", *Proc. Natl. Acad. Sci. USA* 90:1647–1651.

Nelson et al., 1992, "DNA sequencing of four bases using three lanes", *Nucleic Acids Res.* 20(6):1345–1348.

Northrup et al., 1993, "DNA amplification with a microfabricated reaction chamber", The 7th Int'l. Conf. on Solid State Sensors, Actuators, and Transducers, Yokohoma, Japan, Jun. 7–10, 1993, pp. 924–926.

Press et al., 1988, *Numerical Recipes in C*, Cambridge Univ. Press, section 10.9.

Prober et al., Oct. 1987, "A system for rapid DNA sequencing with fluorescent chain–terminating dideoxynucleotides", *Science* 238:336–341.

Quesada et al., 1991, "High–sensitivity DNA detection with a laser–excited confocal fluorescence gel scanner", *BioTechniques* 10(5):616–625.

Ruiz–Martinez et al., Oct. 1993, "DNA sequencing by capillary electrophoresis with replaceable linear polyacrylamide and laser–induced fluorescence detection", *Anal. Chem.* 65:2851–2858.

Saiki et al., Jan. 1988, "Primer–directed enzymatic amplification of DNA with thermostable DNA polymerase", *Science* 239:487–491.

Sanger et al., Dec. 1977, "DNA sequencing with chain–terminating inhibitors", *Proc. Natl. Acad. Sci. USA* 74(12):5463–5467.

Schober et al., 1993, "Accurate high–speed liquid sample handling of very small biological samples", *BioTechniques* 15(2):324–329.

Schwartz and Ulfelder, Aug. 1992, "Capillary electorphoresis with laser–induced fluorescence detection of PCR fragments using thiazole orange", *Anal. Chem.* 64:1737–1740.

Smith, Feb. 1991, "High–speed DNA sequencing by capillary gel electrophoresis", *Nature* 349:812–813.

Smith et al., 1987, "The synthesis and use of fluorescent oligonucleotides in DNA sequence analysis", *Meth. in Enzymol.* 155:260–301.

Smith et al., Jun. 1986, "Fluorescence detection in automated DNA sequence analysis", *Nature* 321:674–679.

Smith and Thomas, 1990, "Quantitative analysis of one–dimensional gel electrophoresis profiles", *CABIOS* 6:93–99.

Smith, Oct. 1993, "The future of DNA sequencing", *Science* 262:530–532.

Stegemann et al., 1991, "High speed on–line DNA sequencing on ultrathin slab gels" *Nucleic Acids Res.* 49:675–676.

Swerdlow et al., 1994, "Reloading and stability of polyacrylamide slab gels for automated DNA sequencing", *BioTechniques* 16(4):684–693.

Swerdlow and Gesteland, 1990, "Capillary gel electrophoresis for rapid, high resolution DNA sequencing", *Nucleic Acids Res.* 18(6):1415–1419.

Takahashi et al., Apr. 1994, "Multiple sheath–flow gel capillary–array electrophoresis for multicolor fluorescent DNA detection", *Anal. Chem.* 66:1021–1026.

Taylor and Yeung, Aug. 1992, "Axial–beam laser–excited fluorescence detection in capillary electrophoresis", *Anal. Chem.* 64:1741–1744.

Tibbetts et al., 1994, "Neural networks of automated base–calling of gel–based DNA sequencing ladders", Automated DNA Sequencing and Analysis Techniques, Adams et al. (eds.), Academic Press, London.

Tong and Smith, Nov. 1992, "Solid–phase method for the purification of DNA sequencing reactions", *Reprinted from Analytical Chemistry* 64:2672–2677.

Traub, Sep. 1990, "Constant–dispersion grism spectrometer for channeled spectra", *J. Opt. Soc. Am.A* 7(9):1779–1791.

Ueno and Yeung, May 1994, "Simultaneous monitoring of DNA fragments separated by electrophoresis in a multiplexed array of 100 capillaries", *Anal. Chem.* 66:1424–1431.

Veldkamp and McHugh, May 1992, "Binary Optics", Scientific American 266:92–97.

Volkmuth and Austin, Aug. 1992, "DNA electrophoresis in microlithgraphic arrays", *Nature* 358:600–602.

Warner and McGown, Jun. 1992, "Molecular Fluorescence, Phosphorescence, and Chemiluminescence Spectrometry" *Anal. Chem.* 64:343R–352R.

Welsh et al., (1992), "Arbitrarily primed PCR fingerprinting of RNA", *Nucleic Acids Res.* 20:4965–4970.

Welsh and McClelland, 1991, "Genomic fingerprinting using arbitrarily primed PCR and a matrix of pairwise combining primers", *Nucleic Acids Res.* 19:5275–5279.

Williams et al., (1990), "DNA polymorphisms amplified by arbitrary primers are useful as genetic markers", *Nucleic Acids Res.* 18:6531–6535.

Woolley and Mathies, Nov. 1994, "Ultra–high–speed DNA fragment separations using microfabricated capillary array electorphoresis chips" *Proc. Natl. Acad. Sci. USA* 91:11348–11352.

Zhang and MacDonald, 1992, "ARIE process for submicron silicon electromechanical structures", *J. Micromech. Microeng.* 2:31–38 (1992).

Ziegle et al., 1992, "Application of automated DNA sizing technology for genotyping microsatellite loci", *Genomics* 14:1026–1031.

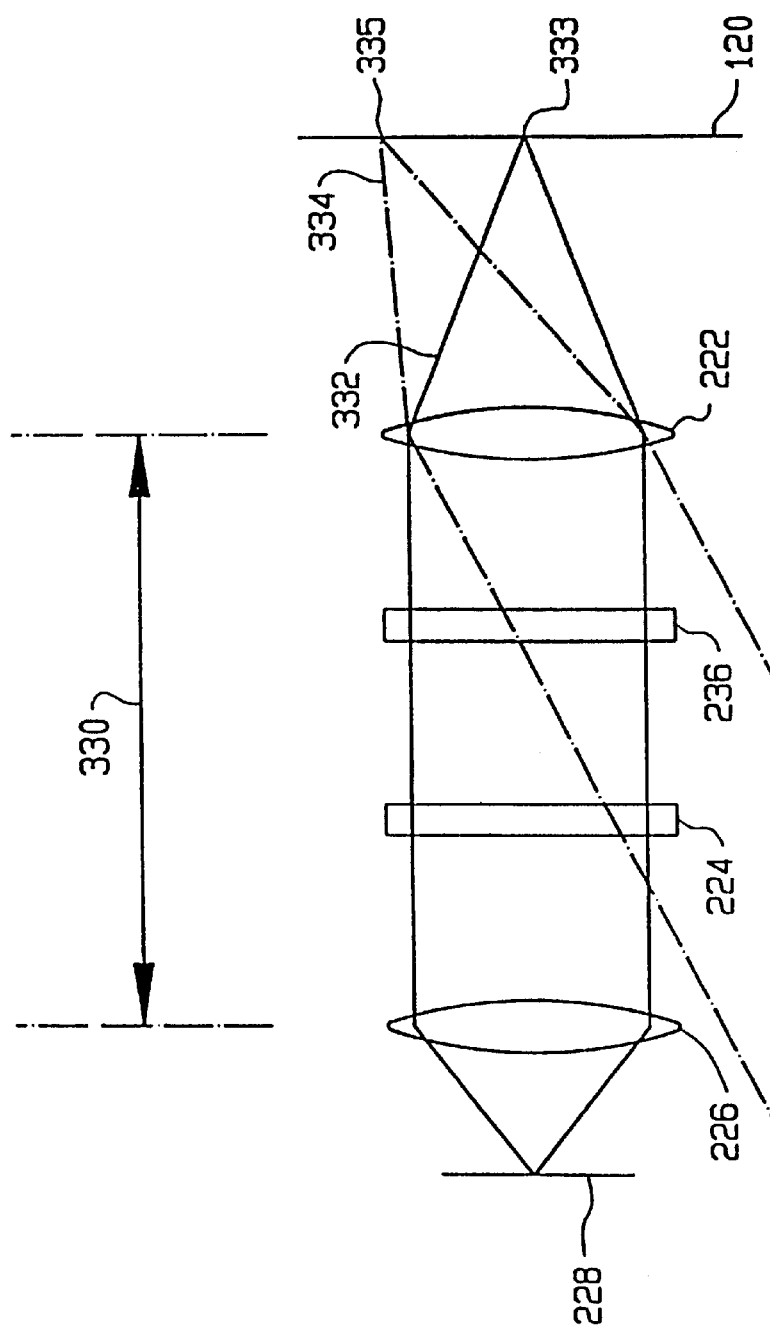

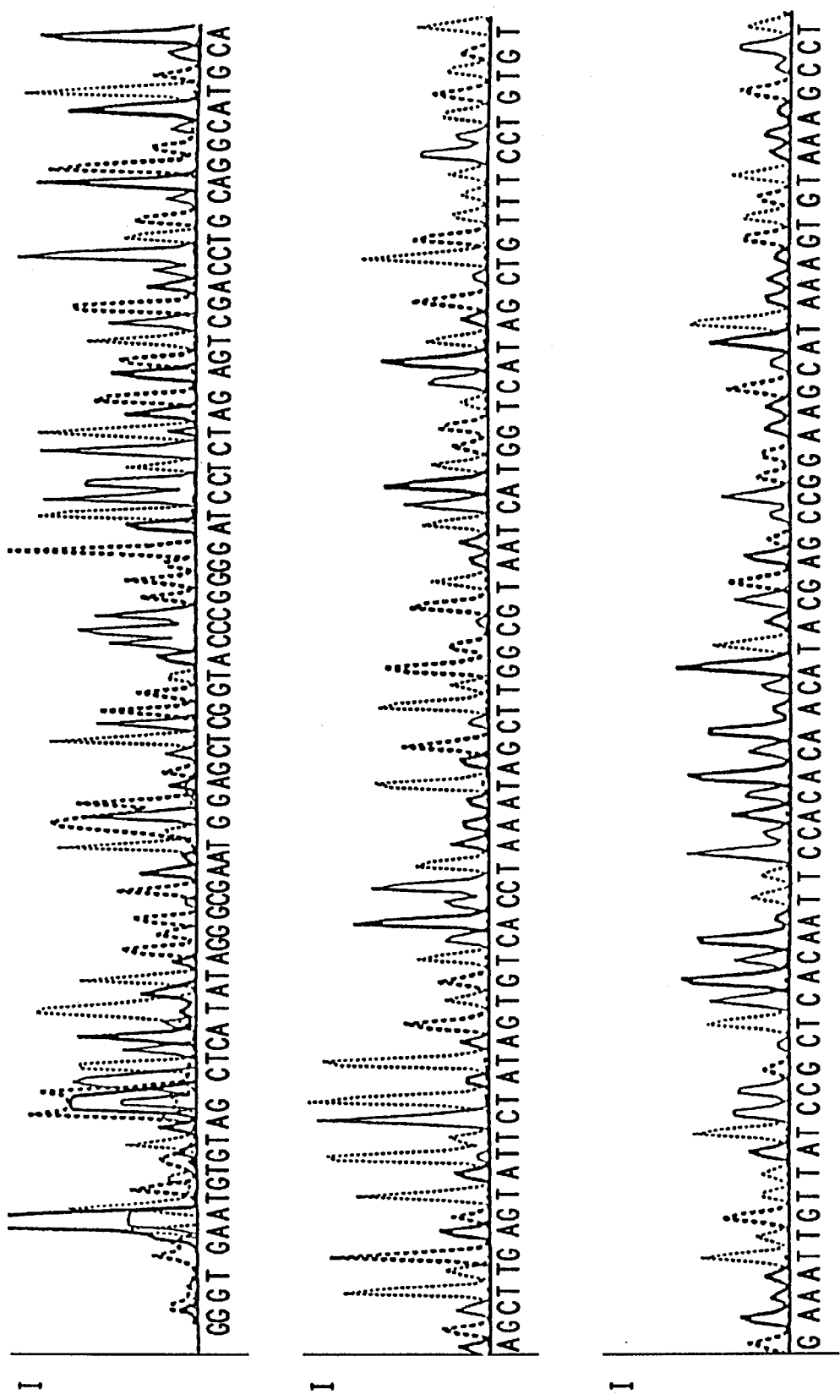
FIG. 17₁

APPARATUS AND METHOD FOR THE GENERATION, SEPARATION, DETECTION, AND RECOGNITION OF BIOPOLYMER FRAGMENTS

This is a divisional application of application Ser. No. 08/438,231, filed May 9, 1995, U.S. Pat. No. 6,017,434 which is hereby incorporated by reference in its entirety.

This invention was made with government support under grant numbers 1R43HG00960-01, 1R43HG01013-01A1, and 1R43CA65184-01 awarded by the National Institutes of Health. The government has certain rights in the invention.

This specification includes a microfiche appendix containing a listing of the computer programs of this invention, this appendix comprising 2 microfiche of 173 total frames.

A portion of the disclosure of this patent document contains material which is subject to copyright protection. The copyright owner has no objection to the facsimile reproduction by anyone of the patent document of the patent disclosure, as it appears in the Patent and Trademark Office patent file or records, but otherwise reserves all copyright rights whatsoever.

FIELD OF THE INVENTION

This invention relates to a method and apparatus for analysis of biopolymers by the electrophoretic separation of biopolymer fragments. More particularly, it relates to a method and apparatus for automated, high-capacity, concurrent analysis of multiple DNA samples.

BACKGROUND OF THE INVENTION

Molecular biology research depends on biopolymer analysis. Conventionally, for this analysis, a biopolymer sample is first fragmented into shorter length biopolymer fragments by enzymatic or chemical means. The fragments are distinctively labeled with detection labels and then separated, often electrophoretically. The fragment pattern is then detected to obtain information about the structure and nature of the original biopolymer sample. These steps are typically performed separately with human intervention required to transfer the sample from one step to another.

A well known example of biopolymer analysis is DNA sequencing. See F. Sanger, et. al., DNA Sequencing with Chain Terminating Inhibitors, 74 Proc. Nat. Acad. Sci. USA 5463 (1977); Lloyd M. Smith, et. al., Fluorescence detection in automated DNA sequence analysis, 321 Nature 674 (1986); Lloyd M. Smith, The Future of DNA Sequencing, 262 Science 530 (1993), which are incorporated herein by reference. A prevalent sequencing method comprises the following steps. A DNA sample is first amplified, that is the DNA chains are made to identically replicate, usually by the polymerase chain reaction (PCR). From the amplified sample, nested sets of DNA fragments are produced by chain terminating polymerase reactions (Sanger reactions). Each chain fragment is labeled with one of four fluorescent dyes according to the chain terminating base (either ddATP, ddCTP, ddGTP, or ddTTP). These fragments are then separated according to their molecular size by polyacrylamide gel electrophoresis and the unique dyes detected by their fluorescence. The DNA base sequence can be simply reconstructed from the detected pattern of chain fragments.

Electrophoresis is the separation of molecules by differential molecular migration in an electric field. For biopolymers, this is ordinarily performed in a polymeric gel, such as agarose or polyacrylamide, whereby separation of biopolymers with similar electric charge densities, such as DNA and RNA, ultimately is a function of molecular weight. The prevalent configuration is to have the gel disposed as a sheet between two flat, parallel, rectangular glass plates. An electric field is established along the long axis of the rectangular configuration, and molecular migration is arranged to occur simultaneously on several paths, or lanes, parallel to the electric field.

DNA sequence information is key to much modern genetics research. The Human Genome Project seeks to sequence the entire human genome of roughly three billion bases by 2006.

This sequencing goal is roughly two orders of magnitude (factor of 100) beyond the total, current yearly worldwide DNA sequencing capacity. Sequencing of other biopolymers, for example RNA or proteins, is also crucial in other fields of biology. Other DNA fragment analysis techniques, such as PCR based diagnostics, genotyping (Ziegle, J. S. et al., Application of Automated DNA Sizing Technology for Genotypeing Microsatellite Loci. Genomics, 14, 1026–1031 (1992)) and expression analysis are increasing in use and importance.

The need for methods to identify genes which are differentially expressed in specific diseases such as cancer is of paramount importance, for both the diagnosis of the disease and for therapeutic intervention. Identification of genes specifically expressed in different diseases will lead to better classification of these diseases with regard to their biological behavior. A molecular understanding of disease progression is fundamental to an understanding of a specific disease. The identification of molecular diagnostics that correlate with variations in disease state, growth potential, malignant transformation and prognosis will have tremendous implication in clinical practice, including the diagnosis and treatment of the disease.

No current method adequately or efficiently addresses the need to identify, isolate, and clone disease-specific genes. A new biopolymer fragment analysis method has been developed based on the use of arbitrarily primed PCR (Williams, J. G., Kubelik, A. R., Livak, K. J., Rafalski, J. A., and Tingey, S. V., DNA polymorphisms amplified by arbitrary primers are useful as genetic markers. Nucleic Acids Res. 18, 6531–6535 (1990); Welsh, J. and McClelland M., Genomic fingerprinting using arbitrarily primed PCR and a matrix of pairwise combinations of primers. Nucleic Acids Res., 19, 5275–9 (1991)). When applied to mRNA, samples are first reverse transcribed into cDNA and then amplified with a combination of arbitrary and specific labelled primers (Froussard, P., A random-PCR method (rPCR) to construct whole cDNA library from low amounts of RNA. Nucleic Acids Res. 20, 2900 (1992); Welsh, J. et al., Arbitrarily primed PCR fingerprinting of RNA. Nucleic Acids Res., 20, 4965–70 (1992)). The resulting labeled DNA fragments are then electrophoresed through a gel producing a "banding pattern" or "fingerprint" of the mRNA source and run in separate gel lanes (Liang, P. and Pardee, A. B., Differential Display of Eukaryotic Messenger RNA by Means of the Polymerase Chain Reaction. Science, 257, 967–971 (1992)). Differences in gene expression are then found by manually comparing the fingerprints obtained from two mRNA sources. Following this, fragments of interest are extracted from the gel. This method is severely limited by its reliance on autoradiographic methods to allow for the isolation of the genes of interest. Refinements of PCR based techniques have, however, led to the ability to produce more reproducible banding patterns, and to the use of an automated DNA sequencing machine to record the banding patterns produced with fluorescently labeled primers (Liang, P., Averboukh, L.

and Pardee A. B., Distribution and cloning of eukaryotic mRNAs by means of differential display: refinements and optimization. Nucleic Acids Res. 21, 3269–3275 (1993)). However, commercial automatic sequencing instruments (Applied Biosystems Inc., Foster City, Calif., DNA sequencer) do not allow for the resolution of many dye labels or allow for the isolation of the fluorescently labeled samples after they are run. In an automated machine the sample is simply lost. Arbitrary primed PCR methods would be much more attractive if their limitations could be addressed.

To address these limitations, our invention allows these gene fragments to be detected fluorescently and to be directly isolated, without human intervention, as they are identified. This is accomplished by electrophoretically separating the individual bands, and hence the differentially expressed genes, from the rest of the sample as it is running. This approach incorporates the advantages of the PCR based methods to differential screening, while raising the level of speed, sensitivity and resolution well beyond that achievable with radiographic techniques. To insure high separation resolution, it is advantageous for the gel throughout a migration lane to be kept as uniform as possible and for the lanes to be sufficiently separated to be clearly distinguishable.

To achieve these required improvements in the analysis capacity for DNA and for other biopolymers, machines are needed for the rapid, concurrent analysis of large numbers of minute biopolymer samples. Further, the analysis must be done with minimal human intervention and at low cost. Since electrophoresis will remain the dominant biological separation technology for the foreseeable near future, the technical demands of more rapid electrophoresis will shape the design of such machines.

More rapid electrophoresis requires, primarily, higher voltages and stronger electric fields to exert greater forces on migrating molecules and move them at greater velocities. However, higher fields and velocities lead to increased resistive heating and consequent thermal gradients in the gel. Gel non-uniformities result, impairing separation resolution. To preserve resolution, ever smaller gel geometries must be used so that this damaging heat may be more readily conducted away. Moreover, parallel, narrow migration lanes are advantageous to increase the number of samples analyzed simultaneously. While electrophoresis has been described in geometries where the parallel glass plates are spaced from 25 to 150 $\mu$m apart, instead of the usual 400 $\mu$m, it is not possible to insure long, parallel, narrow, and closely spaced migration lanes in such a thin sheet. Alternatively, electrophoresis has been described in arrays of capillary tubes down to 25 $\mu$m in diameter which completely define migration lanes. However, although the conventional plate arrangement is relatively easy to load with gel and samples, arrays of capillary tubes are much more difficult to load. Easy loading is advantageous to minimize analysis setup time and human intervention.

The small geometries required by high resolution, high voltage electrophoretic analysis create additional technical demands. Where fluorescent dye fragment labeling is used, sensitive spectral detection devices are needed. These detection devices must respond quickly, since rapid migration presents fragment samples for detection with only slight time separation. Most significantly, rapid parallel analysis of many biopolymer samples requires the detection device to simultaneously detect fragments migrating in separate lanes. Conventional detectors cannot meet these demands. One design uses rotatable filters to select spectral ranges to present to a single active detector element, this assembly being scanned mechanically across all the migration lanes. However, such mechanical single detector assemblies waste most of the available fluorescence energy from the fragment samples, limit detection speed, prohibit simultaneous detection, and slow sample analysis. Use of spectrally fixed filters also limits dynamic adaptation to different detection labels.

While a spatially compact disposition of the migration lanes might permit simultaneous observation, sample loading into the migration lanes prior to an analysis run requires physical access to the migration lanes. Access is easier and more rapid for widely spaced lanes. Conventional, flat-plate techniques have only straight, parallel lanes and cannot accommodate these divergent requirements.

A high throughput analysis machine would generate voluminous detection data representing the rapidly migrating biopolymer fragment samples. Manual analysis of such data is not feasible. To minimize human post analysis checking, these methods should achieve accuracies of 99% or greater. Further, the data would contain fragment detection events closely spaced, even overlapping, in time. Moreover, small electrophoretic geometries and small fragment sizes would generate only weak signals with increased noise. Prior electrophoretic devices, on the other hand, generated only clearly separated detection events with good signal intensities.

Once fragment events are discriminated, the entire data for a run must be assembled to determine the nature of the original biopolymer sample. For DNA sequencing, this is conventional: the bases and their order in the DNA sample are the terminating bases of the fragments in the order of increasing molecular weight.

All the foregoing technical requirements have prevented creation of an integrated machine for rapid, concurrent generation and analysis of large number of biopolymer fragment samples. The need for such a machine is widely felt in such areas as biological research, for example the Human Genome Project, the biotechnology industry and clinical diagnosis.

SUMMARY OF THE INVENTION

The apparatus and method of this invention have for their object the solution of these problems in electrophoretic biopolymer fragment analysis, and in particular, in DNA sequencing. In one aspect, the invention is an integrated, high capacity, low-cost machine for the automatic, concurrent analysis of numerous biopolymer fragment samples. Among its objects are the provision of: easily loaded, simultaneously observable, electrophoretic geometries comprising multiple migration lanes each of the order of 100 $\mu$m and down to 25 $\mu$m or smaller; a spectral detection system which is capable of sensitive, simultaneous response to signals emitted by all the migration lanes and which is dynamically adaptable, without physical intervention, to different dyes, different numbers of dyes, and different coding of fragments with dyes; automatic generation of multiple biopolymer fragments directly on the analysis machine from crudely purified biopolymer samples and bulk reagents (for DNA, sequencing reactions would be automatically carried out); and an automatic data analysis method for transforming time-series of spectral signal to biopolymer sequences and which is adapted to the unique problems of discriminating overlapping and weak fragment recognition events while achieving 99% or greater recognition accuracies.

A high capacity analysis machine according to this invention includes elements for concurrent loading of multiple samples for analysis onto the machine, an electrophoretic module for actually performing the sample separation, a spectrometer capable of simultaneous spatial and spectral resolution and detection of light signals representative of sample fragments as they are separated by the electrophoretic module, and elements for converting the detected signals into the sequence and character of the biopolymer samples analyzed.

Different sample loading techniques are used by different versions of this invention. One technique consists of simply loading small liquid volumes containing fragment samples—manually or automatically—into wells in the electrophoretic medium. More preferable is solid phase loading. Here a comb-like device has teeth which are sized and spaced to fit concurrently into all the sample wells in the electrophoretic medium. Each tooth carries a fragment sample attached by various denatureable binding methods. All the samples are released concurrently when the teeth are dipped into the sample wells. Advantageously, combs may have 50 to 100 teeth for concurrent loading of that number of samples. Notches machined in the comb insertion region can aid the sample loading by aligning the comb with the sample wells.

Most preferable, especially for DNA sequencing, is a reactor array to generate fragment samples from crude DNA and to inject them onto the electrophoretic module. The reactor array comprises an array of micro-reactor chambers each with a minute inlet port and capillary inlet and outlet passages. The capillary passages are controlled by micromachined valves. In one example a bubble, created by heating the capillary fluid, is used to control fluid flow through a capillary tube. The heating is by a resistive micro heating element formed by depositing a resistive thin film in the wall of the capillary. Leads are deposited to conduct current from an external controller to the heating element. To use this array, samples are introduced through the inlet ports; reagents are successively introduced through the capillary inlets; and fragment samples are ejected through the capillary outlets when reactions are complete. Reactions are facilitated by thermal control and heating elements located within each reactor.

Enabling the use of such a micro-reactor array for DNA sequencing is the use of dUTP rich PCR primers, a method of this invention. PCR amplification and Sanger sequencing can proceed sequentially without interference in one reactor by using the enzyme Uracil DNA Glycosylase (UDG). UDG digests dUTP rich PCR sequencing primers into fragments ineffective for initiating chain elongation in the subsequent Sanger sequencing reactions.

Also enabling the use of the microreactor array for DNA sequencing is the use of the enzymatic pretreatment of PCR products using a combination of Exonuclease I and shrimp alkaline phosphatase (United States Biochemicals, Cleveland, Ohio). The activity of both of these enzymes in PCR buffer eliminates the need for buffer exchanges. The Exonuclease I enzyme removes the residual PCR primers, while the shrimp alkaline phosphatase de-phosphorylates the dNTP's inactivating them. The removal of both the primers and excess dNTP's prevents them from interfering in the subsequent Sanger sequencing reactions.

Enabling the use of the microreactor array for other DNA fragment analysis methods including expression analysis, genotyping, forensics, and positional cloning is the direct incorporation of fluorescent labels onto the 5' end of the original PCR primers. These primers can be either specific for known sequences, as in the case of genotyping or arbitrary as in the case of expression analysis. A series of different dyes can be used to allow the PCR amplification step to take place in a multiplex fashion within a single reactor.

Once the samples are loaded, separation occurs in the electrophoretic module. The invention is adaptable to use different such modules. One such module comprises rectangular plates spaced slightly apart to define a rectangular sheet of electrophoretic medium. Migration occurs in straight, parallel lanes through this medium. Another version uses ultra-thin plate spacing, down to 25 $\mu$m, and high electrophoresis voltages, thereby achieving rapid fragment separation.

The preferred electrophoretic module is constructed using two plates with a photolithographically generated formation of grooves bounded by the plates. Numerous non-intersecting grooves etched or otherwise formed on the top plate, together with the bottom plate, define the migration lanes. The lanes are therefore separate non-communicating channels for holding separation medium. Different groove and migration lane geometries are possible. One geometry is straight, parallel lanes. The preferred geometry spaces lanes widely at the loading end of the module, to ease the physical aspects of loading, but converges the lanes closely at the detection end, to permit simultaneous detection of separated fragments in all lanes. Groove size may be down to 25 $\mu$m to allow high voltage rapid electrophoresis. The grooves are preferably fabricated with standard photo-lithography techniques and, if necessary, subsequent etching and coating. Various combinations of substrates and processes are available including patterning insulators on conductive surfaces, patterning polymers on insulating/conductive surfaces, or patterning conductors and coating with insulators.

In all versions the highest allowable electrophoretic voltages are used, where the maximum voltage is determined as that at which the mobility of biopolymer fragments is no longer sufficiently length dependent. Thermal control is achieved with a thermal control module in good thermal contact with the bottom plate. The preferred electrophoresis module provides especially good thermal control, since the small separation medium channels are in close contact on all sides with top and bottom plates. The thermal control module has a heat sink adapted to heat exchange with an air or water exchange fluid. Between the heat sink and the bottom plate of the electrophoretic module are bi-directional heat transfer devices. Preferably these are Peltier thermoelectric modules disposed for pumping heat in both directions. Thereby, the bottom plate can be heated and cooled as needed and thermal gradients eliminated.

In one version, a transmission imaging spectrograph is used to detect separated fragments. The invention is particularly adapted to DNA sequence or other DNA analysis methods, in which each of the different fragment types is labelled with a different spectrally distinctive fluorescent dye. A laser at the separation end of the electrophoresis module excites the dyes to emit light. Emitted light from samples in the migration lanes is incident on a collection lens. The light then passes first through a laser light filter, then through a transmission dispersion element, which spectrally separates the light, and finally through a focusing lens. The focused light is incident on a charge coupled device (CCD) array which detects the simultaneously spatially focused and spectrally diverged light from the detection regions of all the migration channels. Electronic signals from the CCD array provide information about the character or sequence of the DNA sample.

In the preferred version, a microfabricated set of components replaces the large scale imaging spectrograph. Here the function of the two camera lenses and diffraction grating is integrated within a single binary optic diffractive element. The diffractive element can be fabricated either on a glass surface, or on a separate material to be inserted between glass pieces.

The analysis system converts the electronic signals into biopolymer information which in one example is DNA base sequence. It comprises a standard programmable computer with short and long term memory and loaded with analysis programs particularly adapted to the preferred version of this invention. Interface devices place the electronic CCD output signals in the computer memory as binary signals. These signals are grouped both into spatial groups, one group for each migration lane, and into spectral groups, one group for each spectrally distinctive dye label. The grouped signals are filtered to minimize noise: high-pass filtering removes baseline low frequency noise, and low-pass filtering removes high-frequency single spike noise.

The filtered signals are then compared to fragment recognition prototypes and the best prototype is chosen for each segment of filtered signals. The best prototype is that prototype whose averaged signal behavior for nearby times is closest to the observed signal behavior for the same nearby times. Closeness is simply measured by the ordinary distance between the observed signals and the prototypes. The base generating the input signals is identified as the base associated with the closest prototype. The sequence of closest prototypes thereby determines the DNA sequence and this sequence is output from the analysis system.

The prototypes are the averages of filtered signals generated in the apparatus of this invention from the analysis of known DNA. They are carefully chosen to be adapted to the characteristics of this invention. Preferably, they are chosen to include the signals generated by two sequential DNA fragments.

Further analysis is done in one embodiment of the invention. Any DNA sequences which are known (vector DNA) are trimmed out of the observed sequence. The remaining sequence is proofread by Monte Carlo simulated annealing. At random observation times a random alteration to the determined base sequence is made. The closeness between the entire resulting sequence and the entire filtered observed signal is evaluated. If a probabilistic test based on this closeness is met, the sequence alteration is retained; otherwise it is discarded. Alter and test activity is repeated until no further significant improvements occur. This step permits global improvements to be made in the overall sequence determined.

BRIEF DESCRIPTION OF THE DRAWINGS

These and other features, aspects, and advantages of the present invention will become better understood by reference to the accompanying drawings, following description, and appended claims, where:

FIG. 3 shows a ray trace of the transmission imaging spectrograph of FIG. 2;

FIG. 17 shows a recording of an illustrative output of the invention;

DETAILED DESCRIPTION

Instrument Overview

Figure 1:
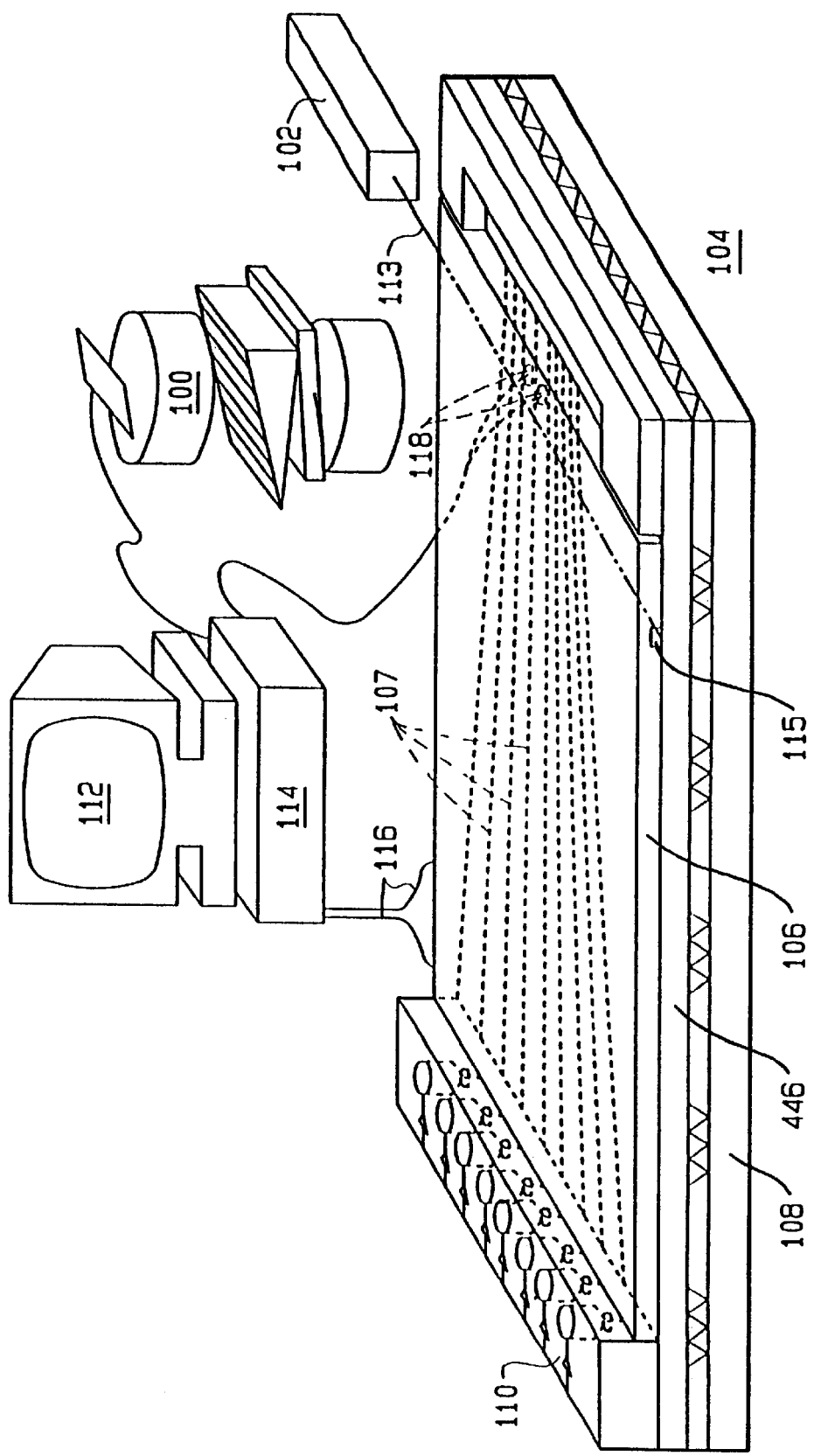
FIG. 1 shows an overall view of a preferred embodiment of the invention.

FIG. 1 illustrates a preferred embodiment of the integrated biopolymer analysis instrument of the invention. Only essential components are depicted; non-essential mechanical components conventional in instrument design are not depicted. The following is a general description of the instrument and its use. Detailed descriptions of the construction and use of components follow.

Element 104 is an electrophoresis module. As illustrated, it comprises a micro-fabricated gel electrophoresis plate (microFGE) 106, a micro-fabricated reactor array (microFRA) 110, and a temperature control subunit 108. MicroFGE 106 comprises converging electrophoresis migration lanes 107 formed as grooves in a glass plate and containing separation medium. Biopolymer fragments differentially migrate in these lanes from left to right under the influence of an electric field supplied by driving electrodes (not shown) at opposite ends of the electrophoresis module. In other versions, the microFGE could have lanes of other geometries, for example, parallel lanes. It could also be replaced with a conventional non-grooved glass plate. MicroFRA 110 is the source of samples of biopolymer fragments for analysis. The samples are generated from raw biopolymer samples in the micro-reactors of the array and loaded directly into the electrophoresis plate typically with a different sample in each migration lane. Illustratively, the fragments are labelled with one of four fluorescent dyes according to the chain terminating base (either ddATP, ddCTP, ddGTP or ddTTP) as is known in the art. In other versions, the microFRA could be replaced with a solid or liquid phase loading apparatus.

At the right is a laser 102 that generates a collimated beam 113 that is directed to pass transversely through the microFGE in an unobstructed laser channel 115. The terminal ends of the migration lanes 107 intersect this channel. The beam thereby simultaneously illuminates the separated biopolymer fragments in the different migration lanes and excites their labels to fluoresce. A transmission imaging spectrograph 100 is disposed above the beam. The spectrograph has within its field of view all the converged migration lanes in microFGE 106 and is equipped to make simultaneous spectral observations of fluorescence in all of the migration lanes. Light resolved by the spectrograph is converted into electronic signals representative of the different fluorescent labels that are excited. As a result, the separated biopolymer fragments are detected.

Electronic signals representing these observations are read into a controller/power supply 114 for on-line or off-line processing by a computer 112. The computer performs an analysis adapted to the characteristics of an individual biopolymer analysis instrument and its particular running conditions. The analysis method generates information characterizing the original biopolymer samples, for example DNA base sequences.

Optionally, the computer can also control an analysis run by commanding the controller/power supply to generate necessary voltage outputs. For example, controller/power supply 114 generates the high voltages applied through leads 116 to the driving electrodes to drive molecular migration in the electrophoresis module. If the microFGE has the optional capability to shunt fragment samples between migration lanes as described below in conjunction with FIG. 7, the controller/power supply also generates necessary shunting voltages which are applied to shunting electrodes 118 in the microFGE module.

Transmission Imaging spectrograph

Figure 2A:
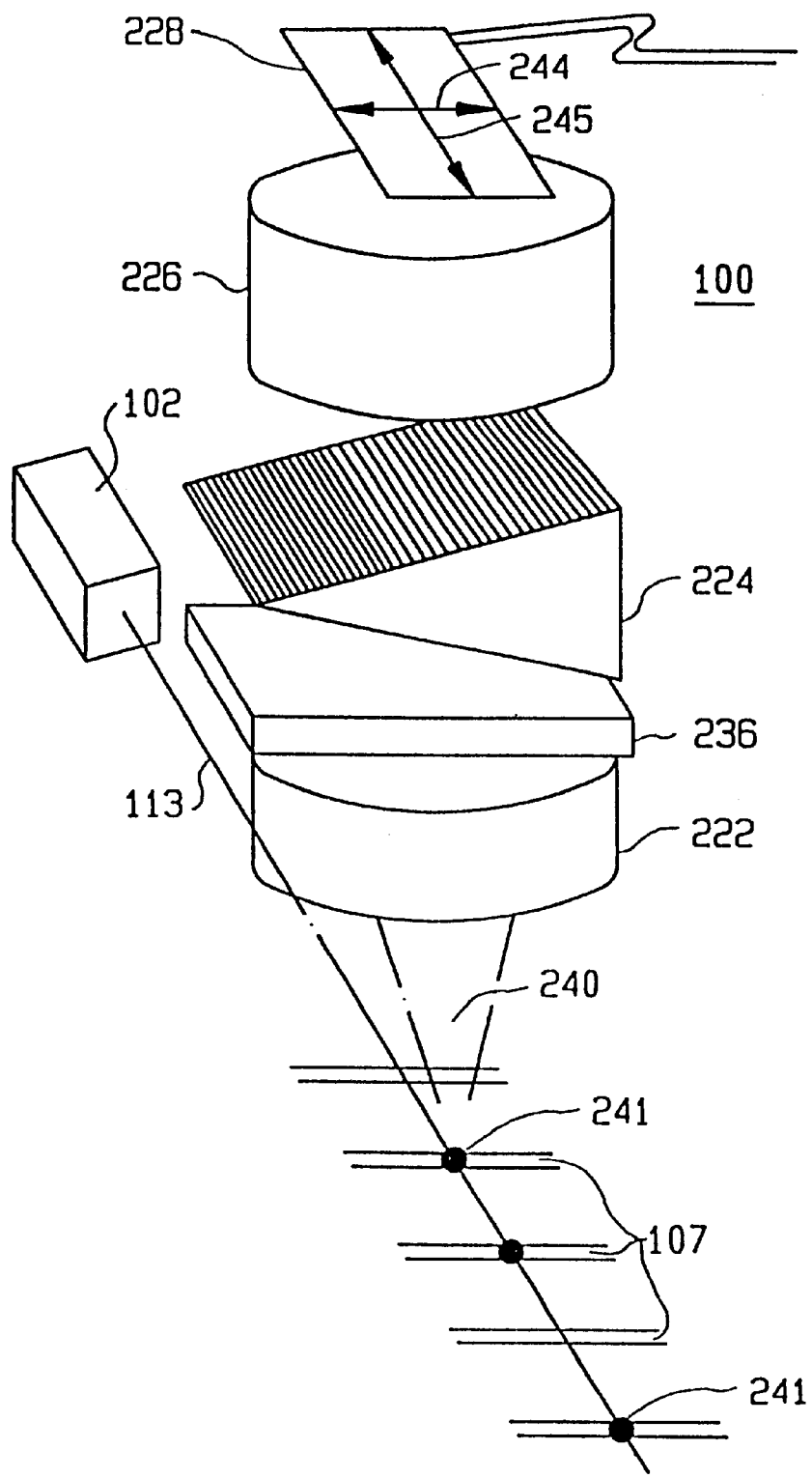
FIG. 2A shows details of the transmission imaging spectrograph that may be used in the device of FIG. 1.

The transmission imaging spectrograph 100 is designed to resolve spectra within the range of common dye labels used in biopolymer analysis (approximately 500 nm to 700 nm), to have high light gathering ability, and to have a wide field of view with little light loss for peripheral images. These features permit the simultaneous viewing of many migration lanes. Advantageously, spectrograph 100 may have a spectral range on the order of 400 nm to 800 nm. FIG. 2A illustrates one version of this component. Non-essential mechanical components conventional in instrument design are not depicted.

As indicated previously, laser 102 generates laser beam 113 which is directed through laser channel 115 so as to intersect electrophoresis migration lanes 107. Light is scattered from this beam primarily by two mechanisms. First, there is some scattering at the laser wavelength by the separation medium and other matter traversed by the beam. Second, when a labeled fragment passes through the beam, it is excited and fluorescence at characteristic wavelength(s) is emitted in all directions.

A portion 240 of this scattered light is incident on spectrograph 100. Spectrograph 100 comprises a collection lens 222, a laser rejection filter 236, a transmission dispersion element 224, a focusing lens 226 and a charge coupled device (CCD) array detector 228. The CCD array comprises a two-dimensional array of CCD detector elements oriented with its short axis along spectral divergence axis 244 and its long axis along spatial focusing axis 245. This orientation gives adequate spectral range and maximal spatial range. Electronic data output from the CCD is transferred to the controller/power supply.

Collection lens 222 collimates the scattered light into parallel rays. Collimated light then passes through laser rejection filter 236, which absorbs light at the laser wavelength. The remaining filtered light, which consists essentially of fluorescence from the fragments, then passes through transmission dispersion element 224, which can be either a grating prism (known as a grism), as illustrated, or alternatively a transmission diffraction grating. This element separates the light into rays of differing wavelength, which diverge along the direction of spectral axis 244. Focusing lens 226 then focuses the light on CCD array detector 228.

Images of the fluorescing fragments in the different lanes 107 are formed along spatial axis 245 and simultaneously separated by wavelength along spectral axis 244. In this manner, different dye labels in different migration lanes produce different patterns along the spectral and spatial axes and can be simultaneously discriminated.

FIG. 3 illustrates the optics of spectrograph 100, spectral dispersion being out of the plane of the diagram. To maximize the field of view focused on the detector and to minimize loss of light at the edges of the field of view, distance 330, between the collection lens 222 and the focusing lens 226, should be as short as possible. As a result, only extreme off-axis rays such as ray 334 will completely miss detector 228 and the optical parameters of the spectrograph can be selected so that sufficient fluorescence from each of the migration lanes is incident on detector 228 to permit identification of the labelled bases. To achieve minimum distance 330, the wavelength dispersive element is preferably a transmission dispersion element, either a transmission grating or a grism.

The following components are exemplary for one version of the transmission imaging spectrograph. For collection lens 222, a Pentax 165 mm f2.8 lens or a 250 mm f5.6 Sonnar medium format camera lens from Carl Zeiss is used. These lenses are commercial camera lenses for use with medium format photography chosen both for their large numerical aperture and wide field of coverage and to match the demagnification required by the other components in the system. Laser rejection filter 236 is a Raman Edge Filter REF521 from Omega Optical Inc. (Brattleboro, Vt.). It has an optical density of 3 to 4 at 515 nm, a transmission greater then 80% over most of the design spectral range, high absorption near the laser wavelength, and behaves well for light incidence off the optical axis. Transmission dispersion element 224 is a Diffraction Products (Woodstock, Ill.), 3090-84ST transmission grating with: 600 grooves/mm, a large clear aperture of 84 mm×84 mm, a back face single layer $MgF_2$ anti-reflection coating, and best efficiency at 500 nm with a first order grating efficiency of approximately 50%. Focusing lens 226 is a Canon 85 mm f1.2 lens. This is a commercially available 35 mm format camera lens with aspherical elements and special low dispersion glass, allowing the design to be optimized for a very large numerical aperture. The CCD array detector 228 is a Princeton Instruments Inc. (Trenton, N.J.) TE/CCD 1024E Detector with a ST 130 DMA Controller. This array detector is 1024×256 pixels with pixel size 27×27 $\mu$m and operated in multipinned phase mode with fast readout along the long axis. This Grade 1 CCD has a large physical dimension along the long axis which provides the spectrograph with a wide field of spatial coverage (the entire width of the gel) while limiting the demagnification required by the lenses selected. Alternatively, a frame transfer CCD can be used that allows for transfer of an image rapidly to a masked portion of the array for subsequent readout, providing a very rapid rate of sequential image acquisition.

One version of the imaging spectrograph was designed for a spectral range of approximately 510 nm to 640 nm, which spans the fluorescence wavelengths of many dye labels. The one-dimensional grating equation is:

$$n\sin(\alpha) - \sin(\beta) = \frac{m\lambda}{\sigma} \quad (1)$$

where m is the order number, λ is the wavelength (in nm), σ is the groove spacing, n is the index of refraction of the grating material, and α and β are the angles of incidence and diffraction, respectively. For first order (m=−1), 600 groove/mm grating, and 0° incidence angle:

$$\sin(\beta) = \frac{\lambda}{1667} \quad (2)$$

Thus 510 nm light diffracts at an angle 17.8°; 575 nm light at 20.2°; and 640 nm light diffracts at 22.6°. With an 85 mm focal length second lens focused at infinity, and 575 nm light directed to the center of the short axis of the CCD camera, then either 510 nm or 640 nm light (diffracted by 2.4 degrees less or more than 575 nm light, respectively) will strike the CCD array at a distance y in mm where $$\tan(2.4) = \frac{y}{85\,\text{mm}} \quad (3)$$

Computing, y=3.56 mm. This corresponds to 132 pixels in the CCD camera with 27 μm per pixel, just slightly more than the 128 pixels available from center to edge of the short axis.

Thus these components provide a version of the spectrograph with adequate spectral resolution over the spectral design range. If desired, CCD array 228 can be rotated by 90° enabling observation of fluorescence over an extended spectral range from 500 nm to near infrared, but over a reduced spatial range. Optionally, a grating with lower groove density (300 grooves/mm) can be used to increase the spectral range observed while maintaining spatial coverage.

Figure 2B:
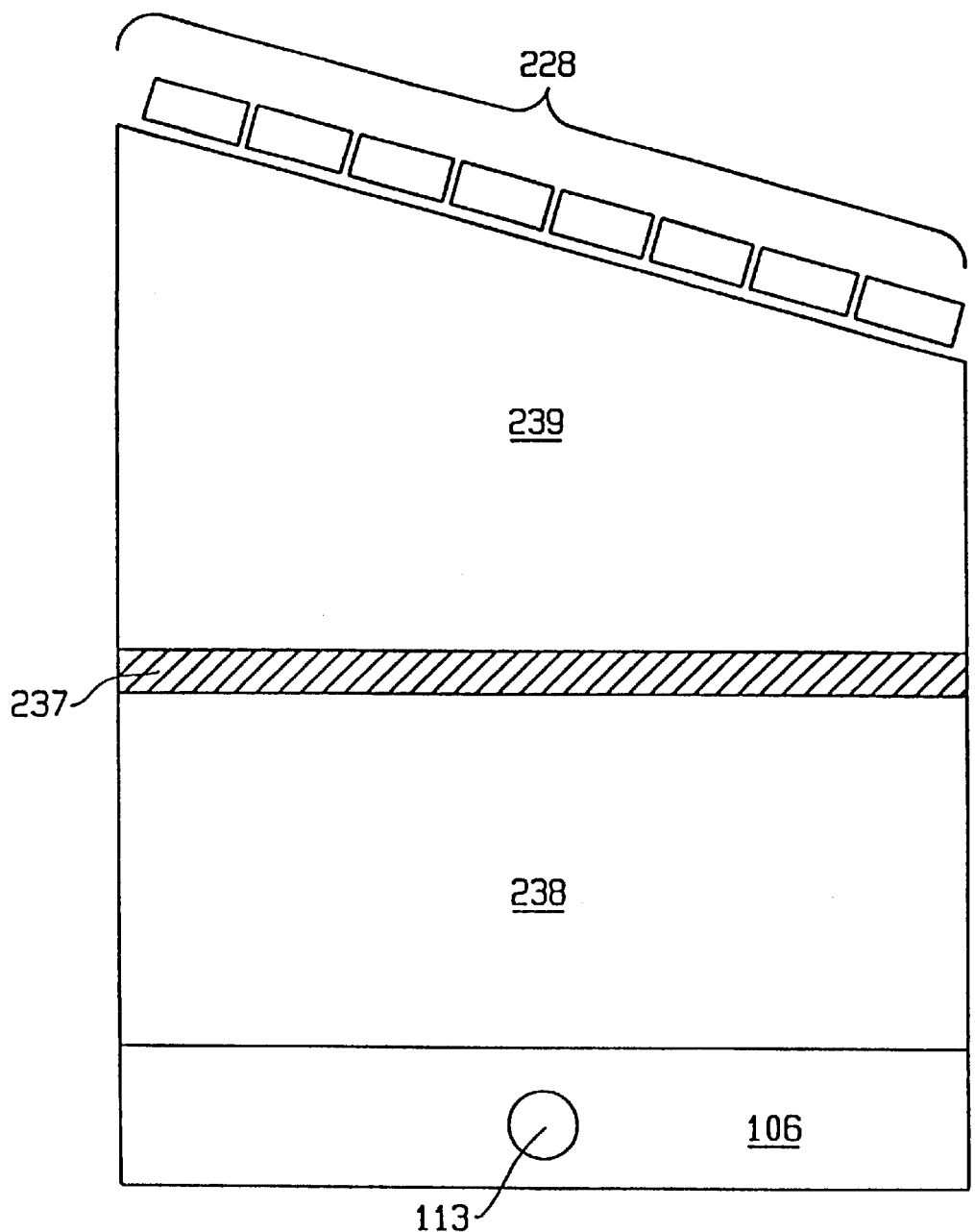
FIG. 2B shows details of an alternative transmission imaging spectrograph of the device of FIG. 1.

Alternatively, the above components can be reduced in size and integrated into a microfabricated imaging spectrograph positioned in contact with a CCD array. A cross-section through one of the many channels of a binary-optic spectrograph array is shown in FIG. 2B. Here the two camera lenses and diffraction grating of FIG. 2A are replaced by a single binary diffractive element 237 located between supporting glass elements 238, 239. This diffractive element can be fabricated on a glass surface as shown or separately on a material to be inserted between glass pieces by conventional photo-lithograph techniques. The fabrication of similar microlenses is known in the art. See, for example, W. B. Veldkamp et al., "Binary optics," *Scientific American*, 266:5, pp. 92–97 (1992) which is incorporated herein by reference. To form the binary diffractive element, SiO2 is typically deposited onto a glass surface and is then patterned using standard e-beam techniques.

Electrophoresis Module

Figure 4:
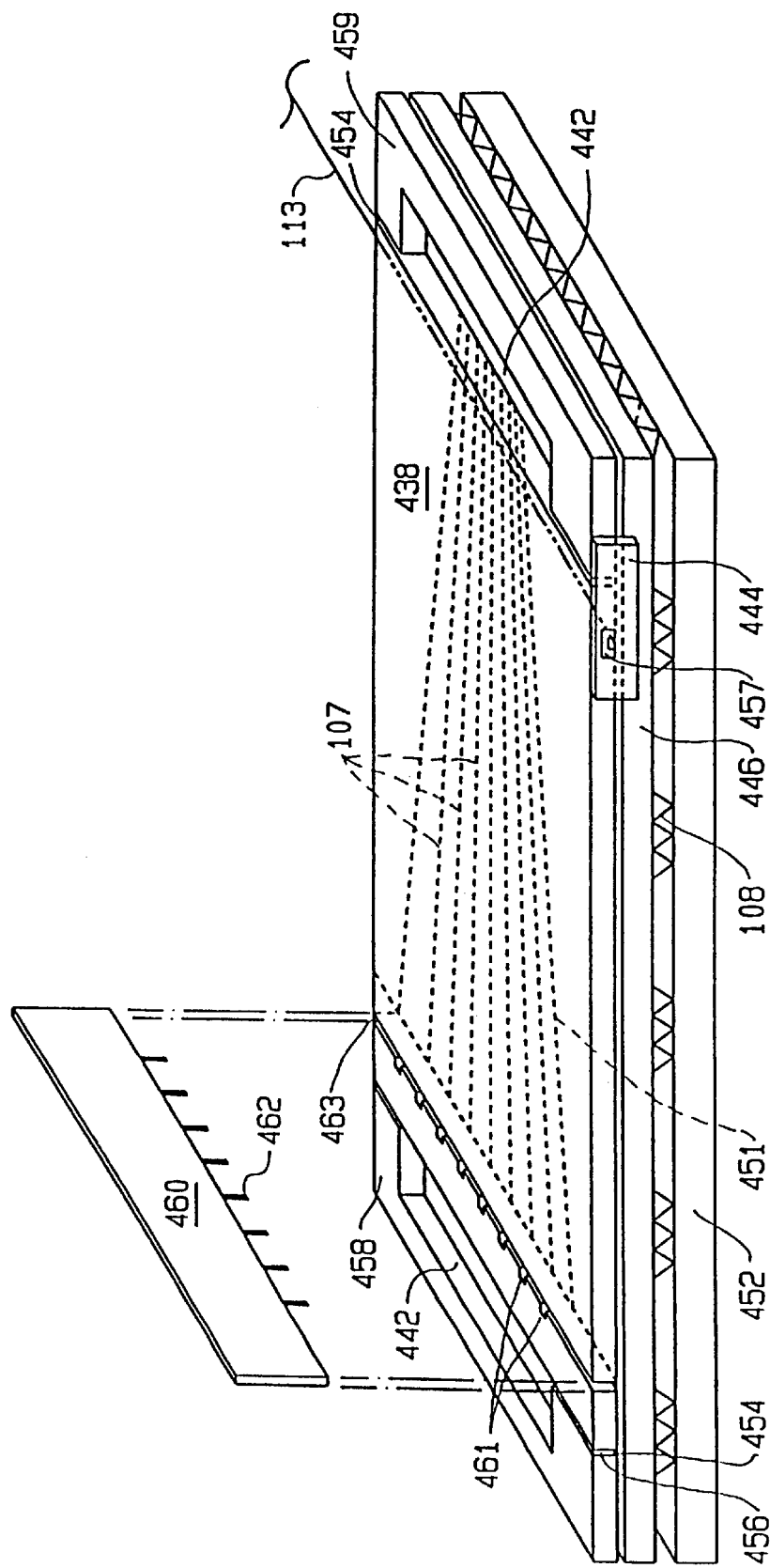
FIG. 4 shows details of an alternative electrophoresis module for use in the device of FIG. 1.

The electrophoresis module is designed to provide a maximum number of small, closely spaced migration lanes, to allow use of high voltages, to dissipate resistive heat, to maintain high resolution, and to be adaptable to alternative sample loading means. Together with the transmission imaging spectrograph, these features promote rapid, concurrent analysis of many biopolymer samples. FIG. 4 illustrates the electrophoresis module. In this figure microFRA 110 has been replaced by a solid phase loading means. Alternatively, a conventional liquid phase loading means may be used. Only essential elements are depicted. Elements conventional in instrument design are omitted. See, for example, U.S. Pat. No. 5,228,971, Brumley et. al., Horizontal Gel Electrophoresis Apparatus (Jul. 20, 1993); U.S. Pat. No. 5,137,613, Brumley et. al., Horizontal Gel Electrophoresis Apparatus (Aug. 11, 1992); and U.S. Pat. No. 5,171,534, Smith et. al., Automated DNA Sequencing Technique (Dec. 15, 1992) which are incorporated herein by reference.

The electrophoresis module comprises a top plate 438, a bottom plate 446, end pieces 458 and 459 and a comb pressure piece 456. Bottom plate 446 provides support and attachment for other module components and serves as the bottom of the migration lanes and buffer wells. Component attachment can be with conventional thumbscrew clamps or other standard mechanical devices. Positioned and attached at the left and right ends of the bottom plate are two end pieces 458 and 459. The end pieces include electrodes for applying high voltage across the migration lanes. The end pieces have a substantially "U" shape, defining buffer wells 442 within the arms of the "U". Buffer solution in these wells is in contact with the separation medium in the migration lanes. The end pieces are sealed to adjacent elements by elastomer seals 454. Left end piece 458 is sealed to comb pressure piece 456, and right end piece 459 is sealed to the right end of top plate 438.

Positioned, attached, and sealed adjacent to the left end piece is comb pressure piece 456. The pressure piece permits liquid communication between the left buffer well and the separation medium. Between the pressure piece and top plate 438 is gap 463 which guides the insertion of a well-forming comb and, optionally, a solid phase loading comb. One such comb is shown in FIG. 4 having a base 460 and numerous teeth 462. The other comb is similar except as noted below. The well-forming comb is used in a conventional manner to form sample loading wells in the separation medium in gap 463. Prior to polymerization of the separation medium, this comb is inserted in gap 463 and fixed in position by a horizontally applied force between the comb pressure piece and top plate 438. This force is conventionally generated by adjustable attachments bearing horizontally against the left end piece 458 so as to bias the pressure piece against the comb. Once the separation medium has polymerized, the well-forming comb is removed leaving sample loading wells at the position of the teeth. In a preferred embodiment, comb pressure piece has machined notches 461 that match the comb teeth 462 to provide rigid formation of wells and aid sample loading.

A solid phase loading comb may also be guided into gap 463 to load biopolymer fragment samples prior to analysis. The teeth of the loading comb are spaced and sized to fit in the sample wells formed by the well-forming comb and, in the case of the preferred embodiment, in the notches machined in comb pressure piece. The teeth have the same center-to-center spacing as those of the well-forming comb but are smaller in size. Fragment samples are bonded to the teeth of the loading comb, the comb is guided by notches 461 into gap 463 so that the teeth enter the sample wells, and the fragment samples are released into the wells. The technique achieves rapid, error free, parallel loading of all the samples for analysis. For further details concerning parallel sample loading, see A. Lagerkvist et al., "Manifold Sequencing: Efficient Processing of Large Sets of Sequencing Reactions," 91 *Proc. Nat. Acad. Sci. USA*, 2245 (1994) which is incorporated herein by reference.

Alternatively, conventional liquid phase loading may be used. In such case, small liquid volumes containing the fragment samples are directly placed into the sample wells. Various conventional mechanical devices may be employed to speed up and reduce errors in this manual process.

The microFGE top plate, illustrated in FIG. 4, includes numerous similar etched migration lane grooves 107 of roughly semi-circular cross section and of diameter between 10 and several 100 μm. The microFGE is positioned and attached in close contact with the bottom plate so that the etched grooves form individual, isolated migration lanes. The lanes are bounded on the bottom by the bottom plate and on the top and sides by semi-circular microFGE grooves. In FIGS. 1 and 4 the etched grooves are illustrated as straight and converging at the laser illumination and detection region. Alternative lane geometries are possible. A preferred geometry includes grooves with first, straight sections that are widely spaced communicating with second sections that converge to a narrow spacing.

Instead of being etched with grooves, top plate 438 may be a conventional glass plate such as a sheet of optical quality glass, such as BK-7, polished to within 1 μm flatness. Such a sheet would be separated 25 to 150 μm from bottom plate 446 by polyester spacer gaskets.

Laser channel 115 is formed from an etched laser groove 457 extending across the plate with a depth not less than that of each of the migration lane grooves. Laser windows 444 cover the ends of the laser groove.

As shown in FIG. 4, a laser beam 113 from laser 102 is directed through channel 115 and illuminates fragments migrating down all the lanes. Alternatively, the laser can be brought into the lane first by directing it through the top or bottom plate and then by causing it to reflect from a suitably positioned mirror mounted within channel 115 so that it propagates through the laser channel. As still another alternative, individual laser sources can be fabricated into each lane by means of known photolithographic processes.

Prior to an analysis run, a separation medium 451 is placed in all migration lane grooves 107 and laser groove 457 to resolve the fragment patterns. Separation medium 451 within the grooves is in contact with liquid buffer in buffer end wells 442. Most separation involves the use of polymer sieving media, either cross-linked gels or linear liquids. Most are based upon polyacrylimide. For example, when unpolymerized polyacrylimide is introduced into the lanes as a liquid, it polymerizes over a few minutes. Rarely is the media reusable and the careful cleaning required is labor intensive.

Alternative separation media are possible with these systems. Recent work has shown that 0.5 micron posts of SiO2 can retard the mobility of like sized DNA fragments (10 kilobases) to enable size sieving. W. D. Volkmuth et al. "DNA Electrophoresis in Microlithographic Arrays," *Nature,* 358, 600 (1992). Reducing the dimension of these posts to the 50 nm size will increase the resolution to nearly base-pair. Another alternative may be offered simply by employing solid polystyrene spheres of an appropriate size. Huber et. al, "High-resolution Liquid Chromatography of DNA Fragments on Non-porous Poly(Styrene-Divinylbenzene) Particles," Nucleic Acids Res., 21, 1061–1066 (1993).

Figure 6:
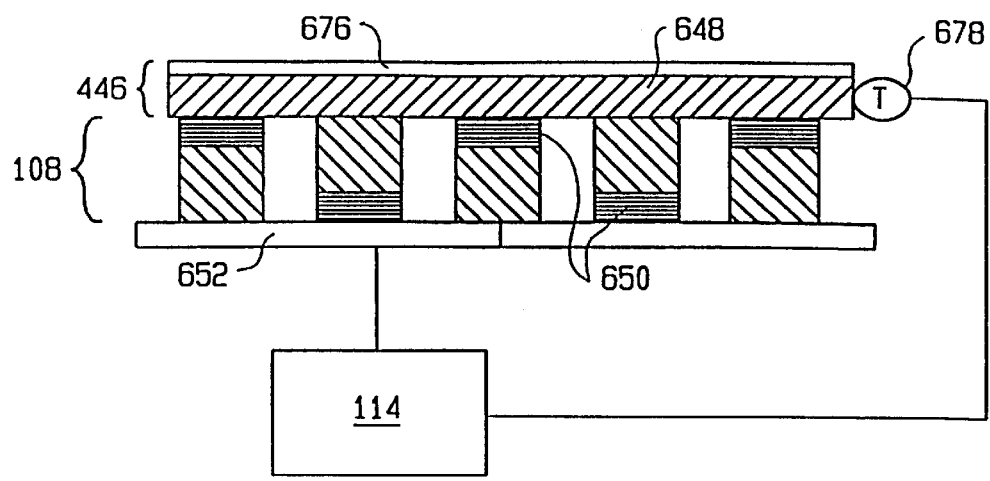
FIG. 6 shows details of the module of FIG. 4.

FIG. 6 illustrates temperature control subunit 108 and bottom plate 446. Bottom plate 446 may be made from a single material, such as glass or sapphire. Preferably it comprises a top plate or coating 676 of a chemically and electrically resistant material, such as a glass, silica, or diamond-like-carbon in substantial contact with a bottom plate 648 made of a highly heat conducting material, such as copper or aluminum. The heat conducting bottom plate may contain conventional water channels or air fins for efficient heat transfer with circulating water or air.

Preferably, the bottom plate is in contact with temperature control subunit 108. This subunit enables precise control of the separation medium temperature and ensures its uniformity. The elimination of injurious separation medium temperature gradients is vital to good electrophoretic resolution. The subunit comprises a heat sink 652 for transferring heat. The heat sink may contain water channels or cooling fins for efficient heat transfer with circulating air or water. A number of Peltier-effect thermoelectric heat pump assemblies 650 are mounted in good thermal contact between heat sink 652 and bottom plate 446. These heat pumps are mounted for rapid bi-directional heat transfer between the bottom plate, and thereby the separation medium, and the heat sink. They are powered by controller/power supply 114 in response to temperature input from thermocouple(s) 678 in contact with the bottom plate. As a result, bottom plate 446 is maintained at a desired, uniform, operating temperature, which may range from ambient to 90° C. The top plate can also be controlled in a similar manner.

Electrophoresis Module: MicroFGE

An industry standard, photolithographic fabrication process is used to fabricate the migration lane grooves and laser groove in the microFGE. A photolithographic mask with an etching pattern is constructed in a standard manner. Two patterns have been used. One has 80 straight, parallel, 11 cm long, 300 μm wide grooves spaced on 1.125 mm centers. The other has, at the left, 80 straight, parallel, 2 cm long, 50 μm wide grooves spaced on 1.125 mm centers, in the middle an angular bend, and at the right, straight, approximately 4 cm long, 50 μm wide grooves converging to 300 μm spacing. At the extreme right of both geometries is a 5 mm wide groove across the plate for the laser channel. Because the etch solution undercuts the etch mask during etching, the actual photolithographic groove width is less than the desired microFGE groove width.

Figure 5A:
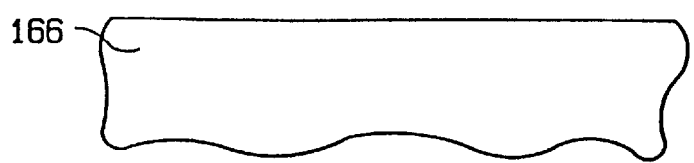
FIGS. 5A–5E show details of the process for making the electrophoresis module of FIG. 4.
Figure 5B:
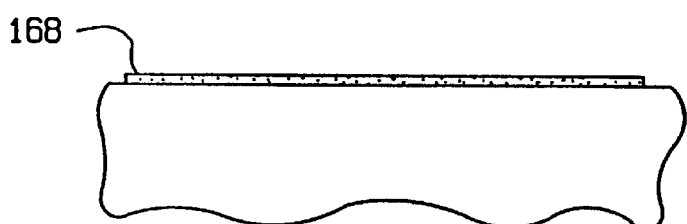

The photolithographic mask is used in a conventional etching process comprising the steps illustrated in FIGS. 5A–5E. The substrate is a 12.7 cm×12.7 cm glass plate 166 polished to less than 1 μm flatness on both sides. Both plate surfaces are first prepared with a standard ammonia/hydrogen peroxide RCA clean. As shown in FIG. 5B, a silicon carbide (Sic) etch mask 168 is deposited using Plasma-Enhanced Chemical Vapor Deposition (PECVD). The reactants are $CH_4$ and $SiH_4$ with flow rates of 65 and 12 sccm, respectively; the power is 50 $mW/cm^2$; and the substrate temperature is 250° C. A five minute deposition on both sides of the glass plate leaves a thin SiC layer. This is followed by a dehydration bake for good photoresist mask adhesion.

Figure 5C:
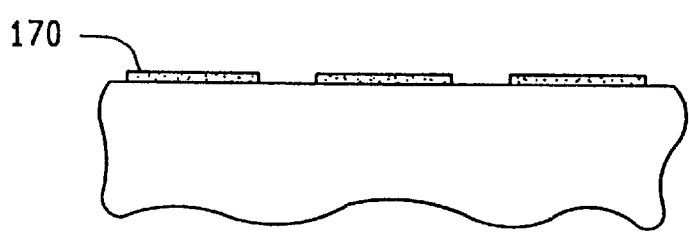
Figure 5D:
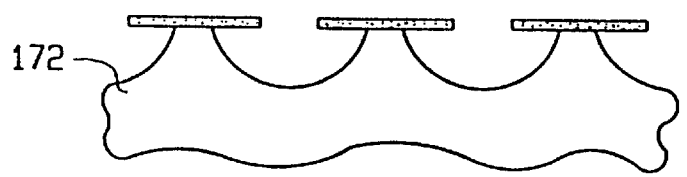
Figure 5E:
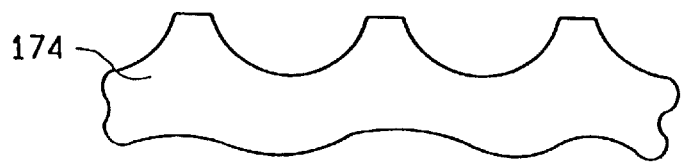

Photoresist is then spin-coated on the front and a similar protective material is applied to the back of the glass plate. Illustratively, the spin-coating apparatus is a Shipley 1813 operating at 4000 RPM. Next, the photoresist is exposed through the photolithographic mask to a total exposure of 200 $mJ/cm^2$ at 405 nm and then developed. As shown in FIG. 5C, the photoresist pattern is transferred to the SiC etch mask using $CF_4$ reactive ion etching (RIE) at 40 mT and 300 $mW/cm^2$ for 7 min. to form a patterned etch mask 170. Over etching insures that no residual SiC remains in the exposed areas. Remaining photoresist is not stripped, as it serves to plug holes and defects in the SiC etch mask. As shown in FIG. 5D, the plate is then etched by immersion in a buffered HF (6:1) etch solution. The solution is stirred. The average etch rate is approximately 0.55 µm/min. A total etch time of 150 minutes yields 75–85 µm grooves. After etching, the plates are rinsed in a second bath of HF, then in $H_2O$. The remaining resist and back-side protective material are stripped (Shipley 1165) and the SiC is removed by RIE in a similar process to that used in defining the patterned SiC etch mask 110. As a result, this process transfers the pattern in the photolithographic mask to a pattern of approximately semi-circular grooves 174 on substrate plate 166.

There are a number of variations on the above method, including both substrate and processing. If an insulating layer on a metal platform is sufficiently thick, then the microFGE pattern may be etched directly into this layer with RIE, and the metal will remain flat (unpatterned). A number of thin insulators can be used. A glass or quartz wafer can be bonded or epoxied to the substrate. Alternatively, a number of standard polymers used in the microfabrication industry include polymethylmethacrylate (PMMA) and polyimide (PI). These can be spin-coated onto flat, rigid heat-conducting substrates such as silicon, copper or aluminum. RIE patterning of polymers is typically done with a very simple chemistry such as $O_2$, and etch rates can be very high. The etched polymer microFGE is coated with PECVD Si or $SiO_2$ to facilitate polymerization of the separation medium. Optionally, a conducting substrate can be patterned directly followed by coating with a thin insulating layer. One can prepare standard microFGE plates etched in silicon similar to existing examples in glass, and coat them both with PECVD $SiO_2$, and PECVD diamond-like-carbon (Diamonex, Inc., Pennsylvania). The coatings will be in the range of 5–20 microns thick.

Electrophoresis Module: microFGE shunting Capability

Micro-fabrication techniques permit the microFGE to be optionally configured with the capability to automatically collect selected biopolymer fragment samples. Samples traveling down a sample migration lane are detected in the laser illumination and detection region and analyzed by the computer implemented analysis method. If a particular sample is of interest, the computer can command that it be shunted into an adjacent, empty collection lane. After the analysis run is complete, the shunted sample can be further analyzed in or eluted from the collection lane.

Figure 7:
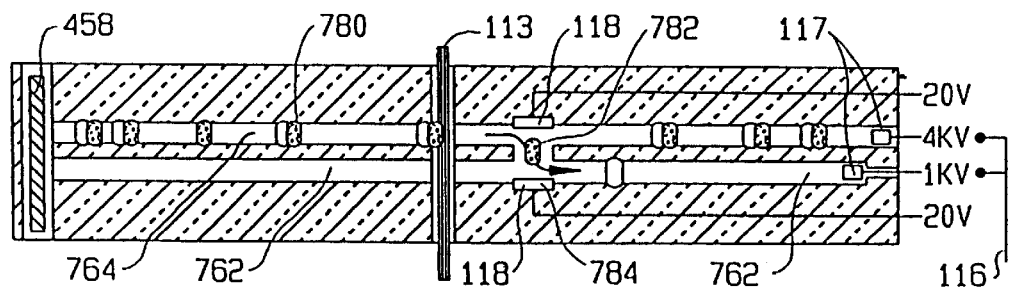
FIG. 7 shows the operation of the module of FIG. 4.

FIG. 7 illustrates two adjacent lanes in the microFGE configured for this biopolymer fragment shunting capability. Adjacent migration lanes 762 and 764 are bounded at one end by end piece 458 and at the other end by driving electrodes 117. Downstream of the laser illumination region is a shunting cross-lane connector 784 with shunting electrodes 118 placed in the walls of the adjacent lanes. The shunting electrodes are connected to and controlled by controller/power supply 114. The cross-lane connector is fabricated by altering the photolithography mask to define the additional etching of the connector. During an analysis run, it contains separation medium. The shunting electrodes are placed by a conventional metallic deposition process.

During an analysis run, biopolymer fragments 780 migrate down the sample lane 764. The fluorescent emission of each fragment is detected as it crosses laser beam 113 and is analyzed by the analysis system. If a biopolymer fragment 782 is determined to be of interest, it is shunted from its sample lane to adjacent collection lane 762 by applying a voltage across shunting electrodes 118 when the sample is adjacent to the cross-lane connector. Sufficient voltage is applied for a sufficient duration to cause migration into the collection lane. The computer commands the controller/power supply to apply voltage at the correct time for the correct duration.

Fragment Generation and Loading: Liquid and Solid Phase Methods

The instrument of this invention is adaptable to a number of generation and loading methods for the biopolymer fragment samples. Liquid phase loading is conventional. This merely requires transferring liquid samples containing biopolymer fragments to sample wells. This is usually a sequential, slow, error prone manual step. Various mechanical and fluid devices may improve speed and error rate. However, it would be advantageous to load multiple samples in one operation in parallel. Even more advantageous would be the capability to generate fragment samples from raw biopolymers and to load them in parallel for analysis.

Figure 10A:
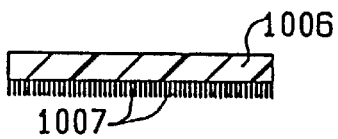
FIGS. 10A–10D show the generation of solid phase fragments in the device of FIG. 1.
Figure 10B:
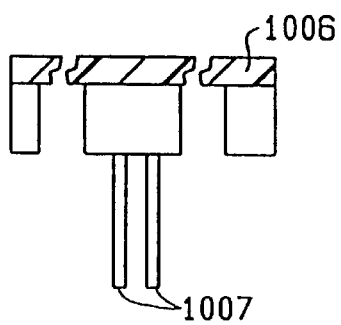
Figure 10C:
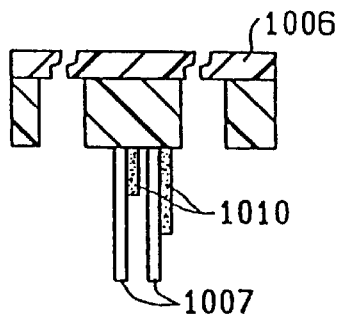

Parallel DNA fragment sample loading can be accomplished by solid phase loading, which is also conventional, although recent, technology. It is illustrated in FIGS. 10A–10D. See Lagerkvist, et. al. (1994). As shown in FIGS. 10A and 10B, a solid-phase loading comb 1006 has 48 or more teeth 1007, advantageously at least 96 teeth. The tips of the teeth are coated with streptavidin. The comb and teeth are designed so that the center-to-center tooth spacing matches the center-to-center spacing of the loading well of the microFGE and all the loading comb teeth can all be inserted into all the loading wells simultaneously. In a preferred method shown in FIG. 4, the teeth of the comb match the spacing of notches 461 machined in comb pressure piece 456 and form robust, mechanically strong, sample wells.

Figure 10D:
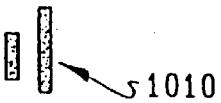

The comb is loaded with biotinylated PCR product samples generated from biotinylated PCR primers. The biotinylated samples are bound to streptavidin coated teeth 1007 by the strong streptavidin/biotin attraction. For example, up to 100,000 copies of a single DNA sample bind to each tooth. Standard Sanger sequencing reactions are then performed on the samples attached to each tooth of the comb to generate DNA fragments 1010 shown in FIG. 10C. The geometry of the PCR and Sanger reactors is advantageously adapted to the comb spacing, so that the comb may be successively dipped in reactors with the appropriate reagents for performing these reactions on all the samples in parallel. The loaded comb with attached fragments 1010 is then dipped in the loading wells and as shown in FIG. 10D the fragments are released from the original sample templates by denaturation, using for example heat and formamide.

Fragment Generation and Loading: MicroFRA

Both the concurrent generation and loading problems are solved by the microFRA 110. The microFRA is an array of chemical micro-reactors for concurrent generation of biopolymer fragment samples for analysis. It is particularly adapted to DNA sequencing. Using any number of single tube (i.e., no separation required) DNA analysis methods, a microFRA can process DNA for analysis directly from minute, unpurified samples. This capability eliminates many manual steps, improving analysis speed and reducing errors. Integrated with the microFGE, a single instrument can perform high-capacity DNA analysis directly from raw DNA samples.

Figure 8:
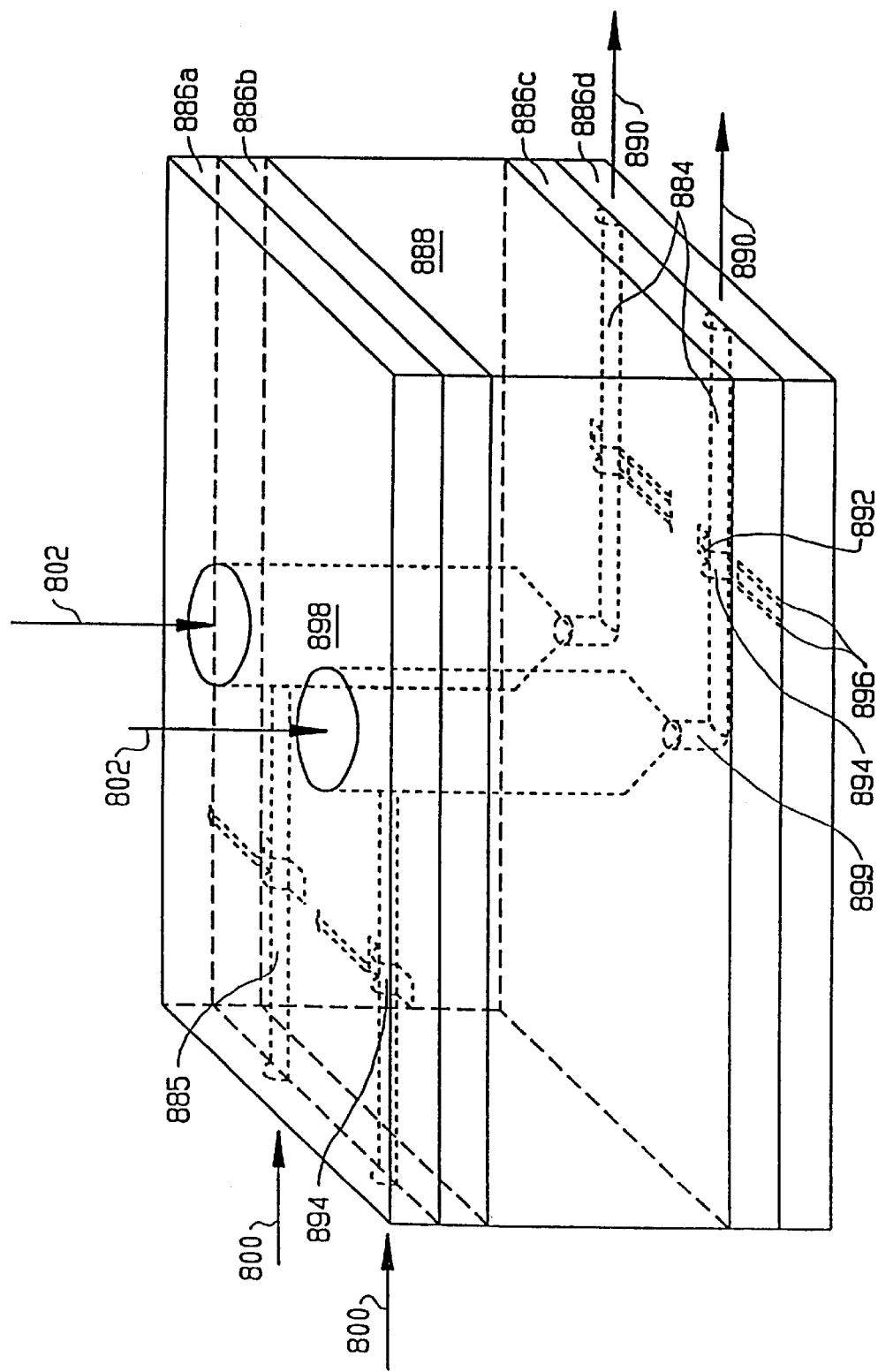
FIG. 8 shows details of an array of two micro-fabricated reactors of the device of FIG. 1.

The microFRA comprises micro-reactors and capillary passages with micro-valves, which control liquid flow in the capillary passages. The construction and use of these elements is illustrated in FIGS. 8 and 9 for the case of a capillary evaporative bubble valve. FIG. 8 illustrates a section of two reactors for one version of the microFRA. Typically, there would be as many reactors as sample migration lanes in the electrophoresis module. MicroFRA structural components include four silicon wafers 886a–d approximately 0.25 mm thick, reactor housing plate 888, preferably constructed from glass and approximately 3 mm thick. Reaction chambers 898 are defined in the structure along with inlet and outlet capillary passages 885, 884. Heating elements and thermocouples, not illustrated, can be incorporated in the walls of reaction chambers 898 for controlling reaction temperatures. Initial biopolymer samples and reagents are introduced into the reaction chambers through minute sample inlets 802. Additional reagents needed during fragment generation are introduced through reagent inlets 800 and capillary inlet passages 885. Biopolymer fragment samples are ejected into the electrophoresis module through outlet capillary passages 884 and fragment outlets 890.

Capillary flow in passages 884, 885 is controlled by several micro-bubble valves 894, which comprise evaporative heating elements 892 and associated electrical leads 896. FIG. 8 shows one valved inlet path and one valved outlet path connected to each reactor. Other versions can be constructed with multiple inlets and outlets to each reactor (such as may be necessary for ethanol precipitation and washing to remove salts, followed by formamide resuspension).

Each reaction chamber 898 is a truncated, conical shaped hole in the reactor housing plate 888 of depth approximately 3 mm, width approximately 1 mm, and volume approximately 1–5 μl. Construction of the microFRA involves etching in top silicon wafer 886a one semicircular capillary inlet passage 885 per reactor with diameter from 5–100 μm, preferably approximately 10 μm. A circular hole, with diameter approximately 1 mm, is formed in alignment with each reaction chamber. The capillary inlet passages terminate in the sides of these holes.

In second silicon wafer 886b, standard deposition techniques are used to deposit micro-heating elements 892, electrical leads 896 to the heating elements, and an electrically insulating layer protecting these components. Each capillary inlet passage is contacted by one micro-heating element. The electrical leads are brought to the edges of the wafer for making contact with external leads from the controller/power supply. The second wafer also has 1 mm holes aligned with those of first wafer and the reaction chambers. The two holes define minute sample inlet 802 into each reactor. The two wafers are bonded together and to reactor housing plate 888 as shown.

The reactor housing plate is bonded to third silicon wafer 886c, which is etched with outlet capillary passages similar to the inlet capillary passages in wafer 886a. Each outlet capillary passage terminates in vertical passage 899 which communicates with the truncated base of one reactor. Fourth wafer 886d, on which are deposited micro heating elements, associated electrical leads, and an insulating layer, similar to those of wafer 886b, is bonded to wafer 886c. Each capillary outlet passage is contacted by one micro-heating element. When the microFRA is positioned, attached, and sealed at the left of the electrophoresis module, as in FIG. 1, the outlet passages communicate with the separation medium at the heads of migration lanes. If a microFGE is used, the capillary outlet passages in wafer 886c could converge so that outlet ports 890 would match microFGE lanes 107.

Preferably, a pressure supply (not shown) is connected to reagent inlet 800 to pressure the capillary inlet passages for introducing reagents during a reaction sequence. Likewise minute sample inlet 802 into the reaction chambers can be connected to a pressure supply for forcing reaction products through the capillary outlet passages to the biopolymer fragment outlets 890.

Fragment Generation and Loading: microFRA Bubble Valve

The evaporative bubble micro-valves 894 are important to the functioning of this version of the microFRA. They provide on/off control of fluid flow in the capillary passages. Alternative micro-actuators of similar function, remote control, and ease of fabrication could be used. [See Lin et, al. Microbubble Powered Actuator, Transducers 1041 (1991).]

Figure 9A:
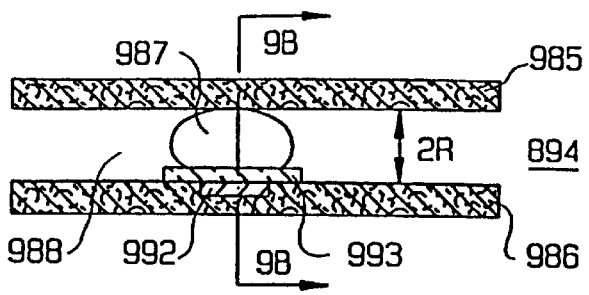
FIGS. 9A–9B show a valve design for the reactors of FIG. 8.
Figure 9B:
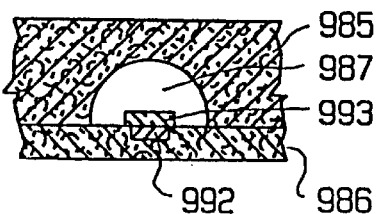

FIGS. 9A and 9B illustrate the construction and operation of an illustrative bubble micro-valve 894. The valve comprises two wafers 985, 986 which are joined together after processing to form the structure shown in FIGS. 9A and 9B. A semicircular capillary passage 988 is etched in wafer 985. A resistive heating element 992 is deposited on wafer 986, and a protective layer 993 is deposited over the heating element to prevent chemical or electrical contact with fluid in the capillary. Electrical leads, not shown, are deposited to provide for external contact. Current to the heating element is supplied through the external contacts and deposited leads from the controller/power supply. Resistive heating element 992, the electrical leads and protective layer 993 correspond to micro-heating elements 892, electrical leads 896 and the electrically insulating layer of FIG. 8 and the accompanying description.

Micro-bubble 987 obstructs the flow of fluid in this passage. It is generated by evaporating fluid in the passage with heat from resistive heating element. Cessation of the heating allows the vapor to cool and condense, collapsing the bubble, and removing the obstruction to fluid flow. Thereby an off/on valve is created and controlled by current in the evaporative heating element.

Surface tensions at the fluid/gas interfaces allow the bubble to be maintained in position despite a pressure difference across the bubble. The allowable pressure difference is determined by Laplace's equation $$P_{fluid} = P_{vapor} + \frac{2\sigma}{R} \quad (4)$$

where $P_{fluid}$ is the pressure difference in the fluid in the capillary, $P_{vapor}$ is the saturation pressure, s is surface tension, and R is the radius of the capillary passage. For a pressure difference between 1.5 and 1.0 atmospheres across the bubble, the capillary diameter must be less than approximately 10 μm.

Fragment Generation and Loading: DNA sequencing using microFRA and dUTP digestion By using dUTP rich PCR primers, the microFRA can completely and automatically process DNA samples from crude DNA to labeled DNA fragments ready for separation, and eventually finished DNA sequence. Using such primers, DNA sequencing fragments can be generated simply by the sequential addition of reagents. An intermediate separation step, not easily possible in a microFRA, to remove unreacted PCR primers is not needed. The microFRA in combination with this technique eliminates all manual DNA sequencing steps. Although adapted for a microFRA, this method of making DNA sequencing fragments can be carried out in other reaction configurations.

The dUTP rich outer amplification primers are designed to prime to known vector sequences, are preferably 17–24 nucleotides long, and are synthesized with dUTP in place of dTTP. Preferably, the dUTPs are no more than 6 base pairs apart, with 4–10 dUTPs per primer molecule. The melting temperature of these primers is preferably between 54° C. and 72° C.

Figure 11:
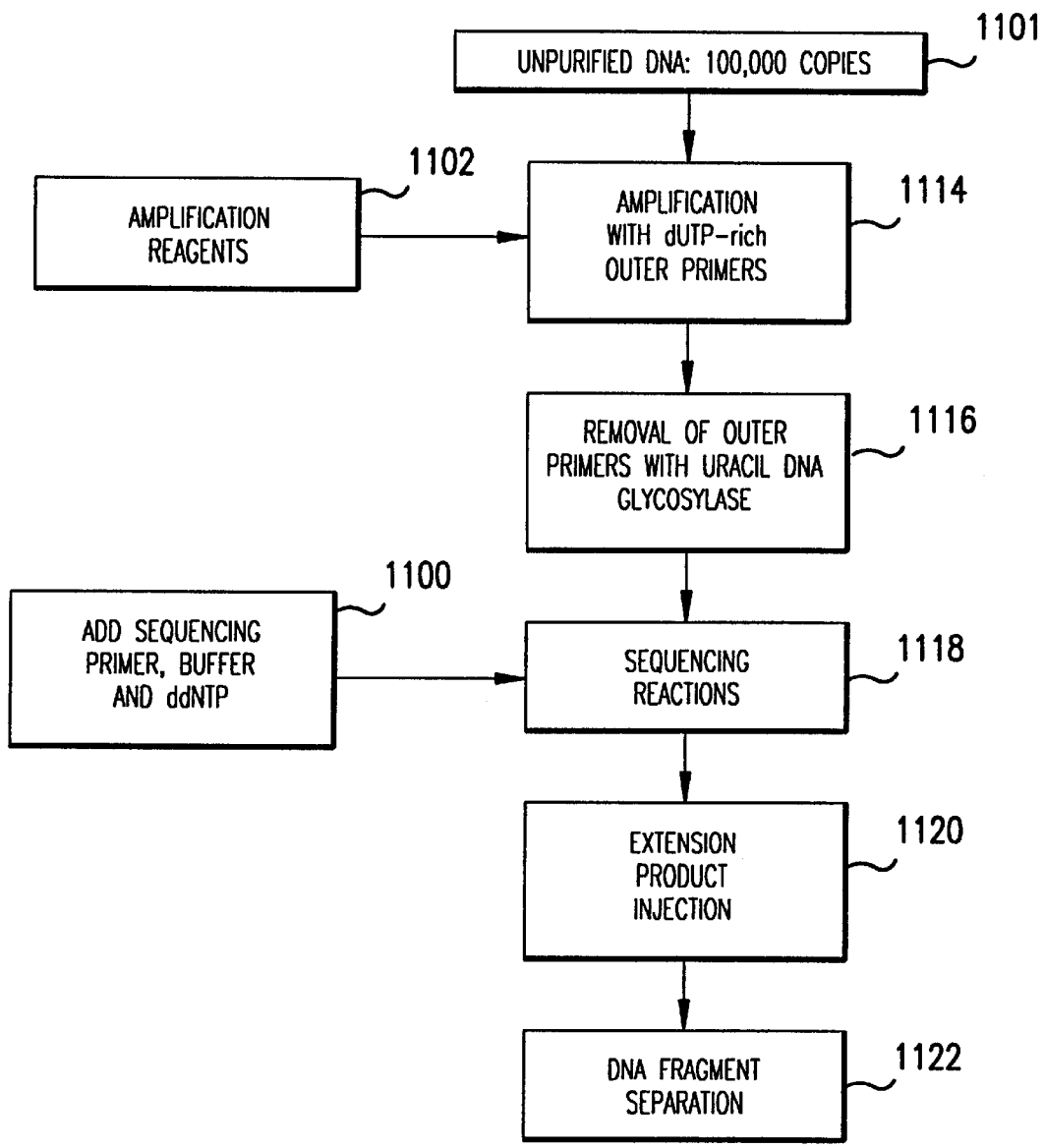
FIG. 11 shows the steps of a dUTP digestion process.

The steps of using these primers are illustrated in FIG. 11. First, at step 1101 10,000 to 100,000 molecules of crude unpurified DNA are loaded into the microFRA reaction chambers through the minute sample inlets. Subsequent reagents can be added either through these inlets or the capillary inlet passages as convenient. No prior DNA preparation is needed. Advantageously, a sterile tip can be used to transfer colonies or other DNA sources containing single or doubly stranded DNA vector with a clonal insert directly into the reaction vessel. Second, at step 1102 amplification reagents are loaded in the reaction chambers. Amplification reagents include: 50–100 picomoles/100 $\mu$l of dUTP containing primer; 75–100 $\mu$molar each dATP, dCTP, dGTP and dTTP; and other conventional reagents such as DNA polymerase, BSA, Ficol, and dye.

At step 1114, twenty to forty amplification cycles are performed. Each cycle comprises the steps of bringing the reaction mixture to 94° C. for 5–15 secs., then to 52° C. for 5 to 15 secs., and then to 72° C. for 15–30 secs.

At step 1116 the dUTP rich amplification primers are removed with UDG, uracil DNA glycosylase, from the Escherichia coli ung gene. UDG removes uracil residues from both single and double stranded DNA present in the reaction mixture. Loss of the uracil residue prevents DNA base pairing and exposes the DNA sugar-phosphodiester backbone to hydrolysis into fragments containing 5' and 3' phosphate termini. The resulting short fragments are no longer able to hybridize to DNA and cannot form a primer for further chain elongation in the following sequencing reactions step.

Next, the reaction mixture is prepared for the sequencing reactions. The mixture is diluted 1 to 10 and a single sequencing primer, buffer and fluorescent dye labeled ddNTPs (step 1100) are added in a conventional manner. Fifteen to thirty sequencing cycles are then performed, each cycle comprising the sequential temperature steps 96° C. for 5–15 secs., 50–60° C. for 1 second, and extension at 60° C. for 4 min. (step 1118). The DNA fragments are next ejected through the capillary outlet passages into the electrophoretic separation subsystem (step 1120). Electrophoretic separation of the DNA fragments then occurs (step 1122).

Fragment Generation and Loading: Expression Analysis

While our system has been designed to be flexible regarding biochemical design, we describe a single exemplary protocol. Recent refinements in molecular biology methods to characterize differences in gene expression makes this possible (Liang et al., 1991). The steps are as follows: (i) mRNA preparation from sample of interest; (ii) first strand cDNA synthesis; (iii) "fingerprinting" by arbitrary PCR of individual samples; and (iv) electrophoresis and fluorescent identification of differences in a single lane.

The high quality of the mRNA is assured by immediate extraction of the mRNA from fresh tissue. The mRNA is extracted from the tissue following a protocol based on the FastTrack mRNA isolation kit (Invitrogen Corp., San Diego, Calif.), which allows transition to purified PolyA mRNA in under 2 hours.

Complementary cDNAs are constructed by using four specific polyT primers; $d(T)_{11}VA$, $d(T)_{11}VC$, $d(T)_{11}VG$, $d(T)_{11}VT$ (V=A,C or G) to prime PolyA mRNA in four separate reverse transcriptase reactions (10 ng/each). This insures that the initial PolyA mRNA pool is broken into four roughly equal portions. By constructing primers with two specific bases at the 3' end the pool could be further divided. These methods utilize extremely small quantities of mRNA (10 ng per reaction). Reaction conditions are designed to minimize any sequence specific bias and to enhance the representation of individual species.

After sample preparation (mRNA isolation and first strand cDNA synthesis), DNA fingerprinting of the individual samples (arbitrarily primed amplification) is conducted using a cycle method based on the use of a thermostable polymerase (PCR). A series of reaction premixes, each containing a specific labeled oligonucleotide primer (one of the four polyT primers with a specific dye attached), a single arbitrary primer, nucleoside triphosphates, and Taq polymerase are added to the first strand cDNA template in an appropriate buffer. Thermal cycling follows, which generates the labeled double stranded family of products (the actual "fingerprint" consisting of 500 to 1000 fragments up to 2 kb in length per reaction).

Primers are designed subject to two major constraints. The first is to insure an even distribution of priming at a specific frequency (determining the number of bands). The second is to insure specificity of the arbitrary primer (insuring reproducibility). In addition, primers are designed by searching against a human sequence database to ensure that they prime at an appropriate frequency (one which will allow for the generation of the most detailed fingerprint that can be characterized within the limitations of our instrument). Arbitrary primers can be designed using mixed bases (A, T, C or G) at the 5' end to allow larger primers to be made, while controlling both melting temperature (all combinations have same melting temperature) and specificity, and with a fixed 3' end (conveniently having a restriction enzyme site to speed up later cloning).

To facilitate the direct identification of the nature of the coding region of the differentially expressed genes, an arbitrary primer strategy which does not utilize the common 3' PolyT primer is used. In this case two arbitrary primers (one of which is labeled) are used for the amplification step.

Analysis Computer and Signal Analysis

Analysis computer 112 is a conventional computer including a programmable processor and both short and long term memory. For example, an Intel 80486 or higher DOS/Windows compatible computer is adequate. An Intel 80486 33 mHz with 16 MB of RAM and 500 MB hard drive is exemplary for both control and analysis. Its control functions required during an analysis run have been previously described. Additionally, it performs the signal analysis which determines biopolymer sample characteristics from a record of the separated fragment samples. The analysis method and apparatus comprises several steps sequentially executed by the processor, each step using input stored in memory and producing output also stored in memory. The data storage memory can utilize either magnetic or electronic memory as appropriate for storing intermediate results between steps. If the microFGE's sample shunting capability is used, data analysis must be done during an analysis run to identify particular samples of interest to shunt. Otherwise, analysis can be done at any time.

The version of the analysis method described and illustrated is directed to determining a DNA base sequence from electrophoretic separation of Sanger sequencing reaction fragments. In this application, four fluorescent dye labels chosen to have distinguishable emission peaks must be recognized. However, the techniques can be applied to analyses of other types of biopolymers.

The analysis method must be adapted to the microFGE electrophoretic module and its running conditions. Because small migration lanes carry small fragment samples, the microFGE generates lower intensity signals with a lower signal to noise ratio than conventional electrophoretic modules. Also, the microFGE's short lanes and high voltages result in more rapid presentation of fragment samples and less clearly defined fluorescence peaks. Further, detailed variations in running conditions due to gel characteristics, voltage used, sample analyzed, and so forth, require that the method be trainable to these variations. These and other characteristics of the microFGE require the uniquely adapted analysis described below in order to achieve better than 99% recognition accuracy.

Figure 12:
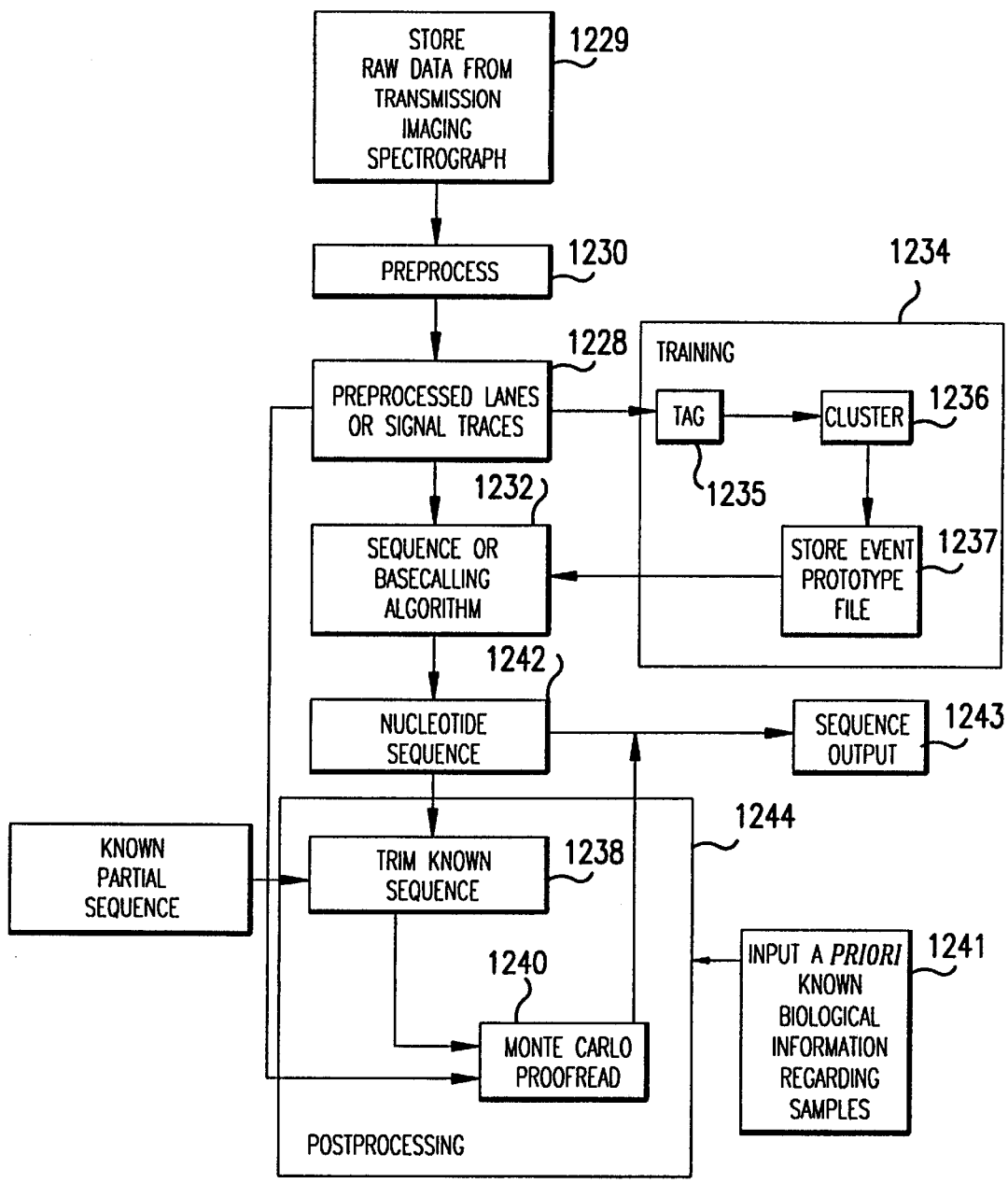
FIG. 12 shows an overall flow chart of the analysis steps used in practicing the invention.

FIG. 12 is a high level flow chart of the analysis. Raw signals from each detector element at each observation time are gathered by transmission imaging spectrograph 100 (FIG. 1) and stored in memory at step 1229. The signal intensity from adjacent detector elements of CCD array 228 may be grouped or summed, called "binning", into sets, called "bins", and the cumulated value of the set reported. Binning done on the CCD array is controlled by software supplied with this component and is dynamically adjustable. Further binning is done by preprocess step 1230. Preferably, 256 spatial bins each spanning four detector elements are defined (the detector having 1024 total elements along the spatial axis). Each migration lane is assigned to one spatial bin, the spectrograph thus allowing simultaneous detection of up to 256 lanes. In the preferred embodiment of the invention, each spatial bin is subdivided into four spectral intensity bins, each spanning 40 detector elements (the detector having 256 total elements along the spectral axis) centered on the emission maximum of the four dyes used to label the four ddNTP bases. Obviously, additional spectral bins can be accommodated by the 256 CCD elements along the spectral axis; and by reducing the number of elements per spectral bin and/or using larger arrays to increase the total number of elements along the spectral axis, the number of spectral bins can readily be increased to about 16 or so, permitting the simultaneous detection of as many different fluorescence signals from different dye labels. The binned signals are further preprocessed at step 1230 by removing recognizable noise and outputting-separately into memory the spectral intensity data for each migration lane for each observation time.

Basecalling step 1232 compares the spectral intensity data for each migration lane for each observation time against an event prototype file.

Event prototype file is generated by training processing at step 1234. For example, a DNA sample whose sequence is known with very high confidence is analyzed in the electrophoretic module by collecting the fluorescence from each of the four fragment labels and generating spectral intensity data that is stored in memory. In particular, the preprocessed spectral intensity sequences from the migration lane with the known sample are tagged at step 1235 with the known base events—A, C, T, G, or the null event X—at the observation times at which the known bases generate signals. This may be done manually or automatically. Then, for all events of each of the different base types, the local time behavior of the signal is averaged, or clustered at step 1236 to generate a prototype intensity signal trace for each event. The prototypes are stored in memory at step 1237 as the event prototype file.

In the preferred embodiment of the invention, event prototypes are determined for pairs of recognition events. Since there are four base events and the null event, there are 16 (=4×4) different pairs of non-null events and therefore 16 different prototype intensity signal traces. Other choices of events are possible with this method.

The basecalling step compares the time series of the reprocessed signals from the spectral intensity bins in a spatial lane 107 with prototype intensity series. If the observed series is judged by some measure to be close to a prototype series, the basecalling step recognizes the base known to be associated with that prototype series. The recognized base identities are output to memory at step 1242 as the nucleotide sequence for that lane 107. This sequence can be finally output at step 1243 or further postprocessed at step 1244.

In postprocessing, if partial sequence information for the DNA sample is known a priori, for example sequences of vector DNA, step 1238 recognizes and trims them from the output sequence. Subsequently a Monte Carlo proofreading step 1240 is executed. Proofreading involves checking the global consistency between the basecalling output and the original unprocessed data. Special knowledge about the DNA being analyzed, for example that the DNA codes for a protein, can also be supplied as at step 1241.

Data Analysis Method: Preprocessing Step

Figure 13:
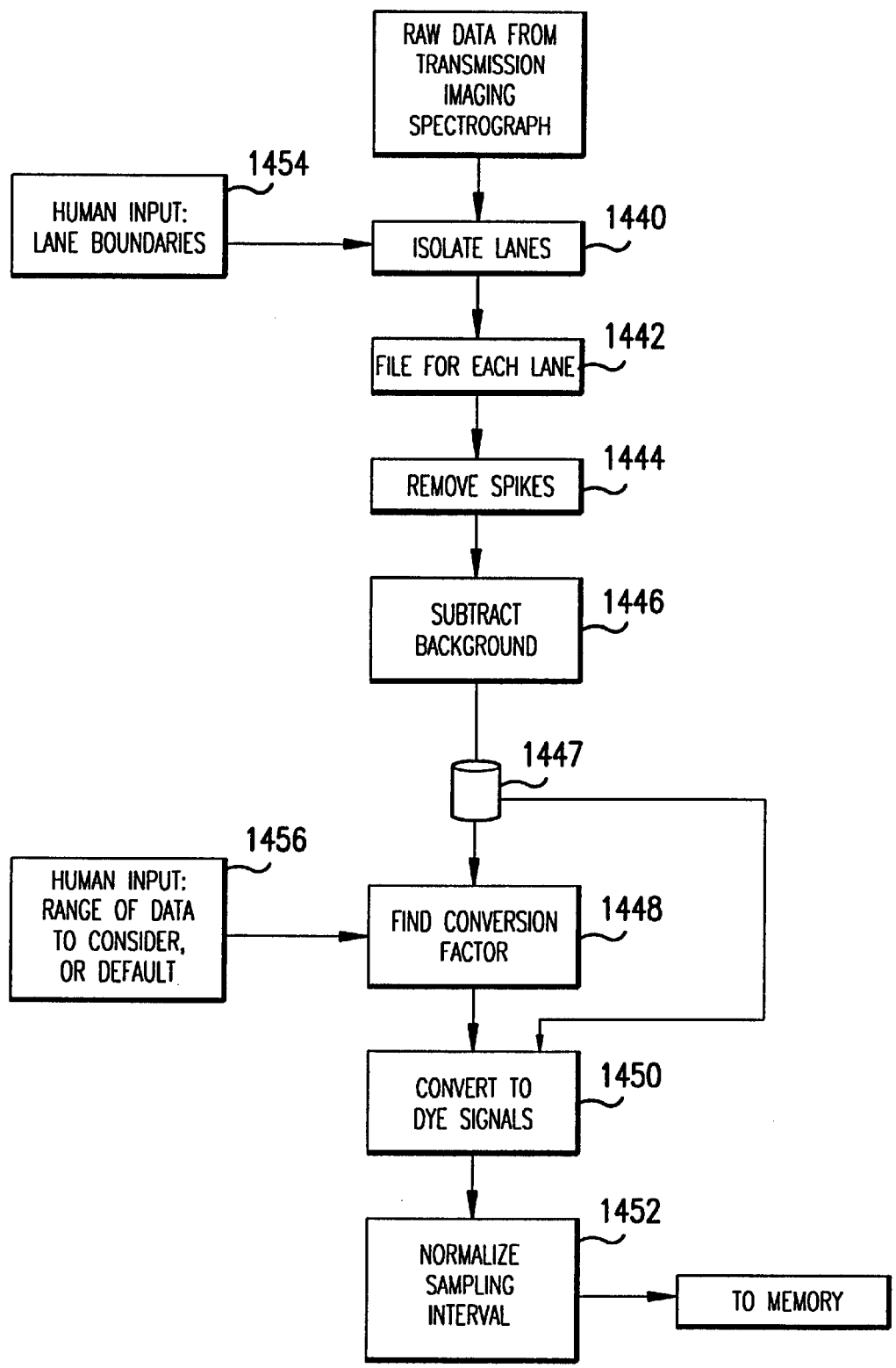
FIG. 13 shows the flow chart for the analysis preprocessor step of FIG. 12.

FIG. 13 is a detailed flow chart of preprocessing step 1230. The input from transmission imaging spectrograph 100 is a concatenation of signals from consecutive exposures of the CCD camera. Each exposure produces binary data representing charge intensities at individual pixels (and accumulated intensities in on-chip defined bins). The pixels are grouped into spatial and spectral bins as previously described, each spatial bin having four associated spectral bins. All further processing is done on these binned signals. First the spatial bin assigned to each migration lane is identified (step 1440) and a file is created in memory for each lane (step 1442). For each migration lane, the operator chooses one of the 256 spatial bins to best represent the fluorescence emitted by samples in that lane. All remaining processing then continues independently for each lane.

Next, for each lane, recognizable noise is removed by high and low pass filtering. Spikes, which are one observation time anomalies, are removed (step 1444) by replacing a signal value in any spectral bin at any observation time with an average of the signal values in the same spectral bin at the preceding and succeeding observation times if the value differs drastically from that average. Next, the background signal is identified and subtracted (step 1446). For each observation time and spectral bin, a background value is computed and subtracted. The background is the best linear fit to the absolute signal minima taken from four windows near the observation time in that spectral bin. The first window contains enough future time points to include preferably about 10 base recognition events (or peaks); the second window enough for 20 future events; the other windows include 10 and 20 past events. The filtered signals are stored in memory at step 1447.

Next, for each observation time, a linear conversion is made from fluorescence intensity signals to signals representative of dye concentration (step 1450). This is done by multiplying the 4 spectral bin values in the data stored at step 1447 by a 4×4 conversion matrix to obtain 4 new values representative of the four dye concentrations. This matrix is determined at step 1448 prior to the conversion in the following adaptive manner. The signals stored at step 1447 are scanned. For a range of observation times from the middle of the analysis run, preferably the middle ½, during which range each signal peak is influenced by a single base event, the three highest peak values are found in each spectral bin. This is done by finding a first maximum, excluding a window around that maximum, then similarly finding a second and third maximum. These peaks are taken to correspond to existence of a single dye in the detection region. (Validity of the assumption is tested by comparing the shapes of the dye emission curves with the ratios of signal intensities in the spectral bins.) For each of the three highest peaks of each of the four dyes, the values in the four spectral bins are obtained. For each bin and each dye the three values are averaged to obtain a set of four numbers that represents the ideal fluorescence signature of that dye. The four signatures are assembled as the rows of a 4×4 matrix. For example, an illustrative signature matrix might be:

| Nucleotide | measured average fluorescence intensity level in bins associated with: | | | |
|---|---|---|---|---|
| | A | T | G | C |
| A | 800 | 100 | 50 | 100 |
| T | 300 | 700 | 100 | 50 |
| G | 100 | 200 | 900 | 200 |
| C | 50 | 50 | 300 | 800 |

The inverse of this matrix is the desired linear conversion factor input to step 1450.

Alternatively, more than four dyes can be employed and a corresponding number of binning regions can be used to accumulate the fluorescence signals from such dyes. In the case that the number of binning regions exceeds the number of dyes, a best-fit linear conversion or pseudo-inverse can be found to determine the dye concentrations.

Finally at step 1452, the signal values at consecutive observation times are added into one new observation and output to memory. Consecutive observations, or larger adjacent groups of observations, are additively combined so that approximately five resultant observation times occur between consecutive base recognition events.

Data Analysis Method: Basecalling step

Basecalling (step 1232) recognizes the event of a labeled fragment in a migration lane passing through the laser beam 113 and discriminates the event into one of a set of classes according to the dye label carried by the fragment. Four initial choices must be made: a configuration space to represent recognition events; a mapping of signal traces into paths in this configuration space; the location of events in the configuration space; and a criterion for determining when the configuration space path represents an event. First, this method is schematically illustrated for a simple case, then the preferred version is described.

Figure 14A:
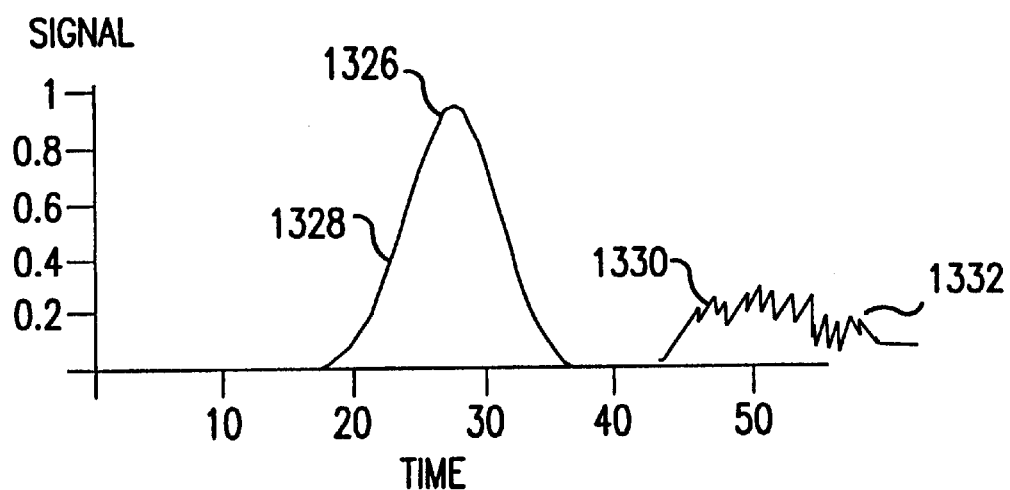
FIG. 14 shows the general operation of the basecalling step of FIG. 12.
Figure 14B:
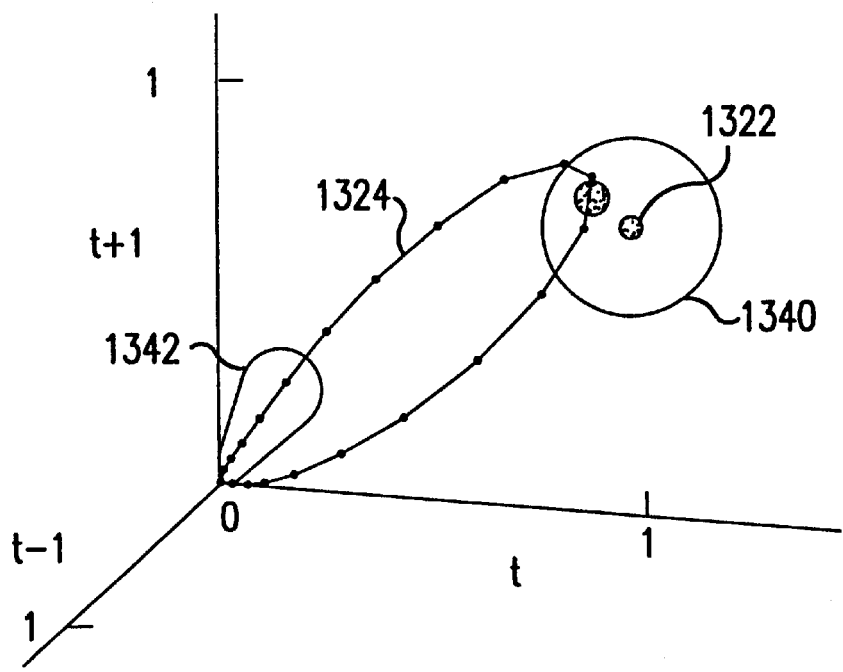

FIGS. 14A and 14B schematically illustrate a simple, exemplary case. In FIG. 14A are two signal traces: one 1328 having a single, tall peak 1326; and a second 1332 having a single, broad, low peak 1330. Trace 1328 represents an event; the trace 1332 represents only noise.

FIG. 14B illustrates the mapping of the signal values at the preceding time point, t−1, at the current time point, t, and at the succeeding time point, t+1, into single 3-dimensional points (t−1, t, t+1) in a 3-dimensional configuration with these three values for coordinates. Thus each point in configuration space represents a triplet of three consecutive signal intensities. Next, based on knowledge of prior event characteristics, an event prototype characteristic of detection of passage of a particular dye label fragment through the laser beam is assumed to be located at 1322. For event recognition, the configuration space path must pass within sphere 1340 about the event prototype.

Signal trace 1328 maps to loop 1324 in configuration space, beginning and ending at the origin and passing, in the example shown, within the recognition sphere. It therefore represents an event. Signal trace 1332 illustratively maps to loop 1342 in configuration space, which does not pass within the sphere. It is therefore not recognized as an event. In this manner, events are recognized and discriminated.

Basecalling step: Embodiment

As indicated in the discussion of FIG. 12, event prototypes are determined for pairs of recognition events, there being sixteen such pairs corresponding to the sixteen doublets of DNA bases—CA, CC, CG, CT . . . TA, TC, TT, TG.

The event recognition criterion is that a local minimum occurs in the distance between the signal trace as mapped into configuration space and one prototype event. Starting from the previous base recognition event, and stepping forward observation by observation, the configuration space distance to each of the 16 prototype events is computed at each observation time. The event identity with the smallest distance and that distance value are saved. If the closest prototypes at the current and adjacent observations are the same, and if the current distance to that closest prototype is less than the distances at adjacent observations, then that prototype is recognized. As indicated above, there are approximately five observation times between successive base recognition events.

In essence the basecalling step measures at a series of observation times following a base recognition event the correlation between the dye concentration values derived from four signals received at the four spectral bins and the corresponding dye concentration values associated with the sixteen doublets of DNA bases that have previously been stored in the prototype file. Beginning with the first observation time following a base recognition event, the measurement is made by calculating a weighted sum of the squares of the differences between five successive time samples of the dye concentration values derived from the four received signals and five successive time samples of the corresponding signals of each of the sixteen doublets, repeating the calculation for the next set of five successive time samples of dye concentration values displaced by one observation time from the previous calculation and the same set of five samples of each of the sixteen doublets, and so on. The distance at the central sample point is weighted highest (2.0); the distances at the previous and succeeding points are weighted intermediately (1.5); and the remaining distances are not weighted (1.0).

The general form of the equation for the weighted sum of the squares is $$(TD_{-2} - TP_{-2})^2 \; + \; 1.5 \cdot (TD_{-1} - TP_{-1})^2 \quad (5)$$
$$+ 2 \cdot (TD_0 - TP_0)^2 \; + \; 1.5 \cdot (TD_{-1} - TP_{-1})^2$$
$$+ (TD_{+2} - TP_2)^2 \; + \; (AD_{-2} - AP_{-2})^2$$
$$1.5 \cdot (AD_{-1} - AP_{-1})^2 \; + \; 2 \cdot (AD_0 - AP_0)^2$$

$$1.5 \cdot (AD_{+1} - AP_{+1})^2 + (AD_{+2} - AP_{+2})^2$$
$$(GD_{-2} - GP_{-2})^2 + 1.5 \cdot (GD_{-1} - GP_{-1})^2$$
$$2 \cdot (GD_0 - GP_0)^2 + 1.5 \cdot (GD_{+1} - GP_{+1})^2$$
$$(GD_{+2} - GP_{+2})^2 + (CD_{-2} - CP_{-2})^2$$
$$1.5 \cdot (CD_{-1} - CP_{-1})^2 + 2 \cdot (CD_0 - CP_0)^2$$
$$1.5 \cdot (CD_{+1} - CP_{+1})^2 + (CD_{+2} - CP_{+2})^2$$

where the first term in each squared expression is the sample of the received signal and the second term is the sample of the stored prototype signal, the letters T, A, G, C identify the relevant dye concentration and the subscript indicates the sample number and its order in time.

The value of the above equation is calculated for each of the sixteen doublets for each of the observation times until a closest prototype is located. Alternatively, however, it is not necessary to make the calculation for twelve of the sixteen doublets because the identity of the first nucleotide in the doublet is already known from the immediately previous basecalling step.

In addition, each calculated value of the sum of the squares is weighted by a factor that increases with the time between the actual observation time and the expected time of the next base recognition event. A match is identified at the observation time where the weighted sum of squares is determined to be lowest.

Further details of the base calling step are as follows: The configuration space is a composite of a 20-dimensional signal-intensity subspace and a 1-dimensional time-from-event-recognition subspace. Signal traces map into the signal-intensity subspace by assigning for the 20 coordinates, sequentially, the four spectral bin values at each of the five observation times—the twice previous time, t−2, the previous time, t−1, the current time, t, the succeeding time, t+1, and the twice succeeding time, t+2. This maps adjacent portions of the signal trace to a 20-dimensional vector in this subspace at the observation time, t. In the 1-dimensional time-from-event-recognition subspace, the coordinate is assigned to the time difference between the current time and the time at the last recognition event.

The distance in the configuration space is the product of distances computed separately in the two subspaces. In the 20-dimensional signal-intensity subspace, the distance is a weighted sum of the squares of the distances (sum of squares of signal coordinate differences) between the signal and a prototype point at the five time points. The distance in the 1-dimensional time-from-event-recognition subspace is the sum of 1.0 and the weighted (0.3) square of the difference between the coordinate value in that subspace and the average time between basecalls.

This precise calculation is illustrated by the following C++ code:

```
class datapoint {
    double c, t, a, g;      /* normalized fluorescence values */
    int tag;                /* call for this data point */
};
class vector {
    datapoint twoprev;      /* data point at current time − 2 */
    datapoint prev;         /* data point at previous time */
    datapoint curr;         /* data point at current time */
    datapoint next;         /* data point at next time */
    datapoint twonext;      /* data point at current time + 2 */
    int lastcall;           /* base last called */
    double timetocall;      /* time since last base call */
    int tag;                /* call for this vector */
};
dist = (
    (
    pow((vec->twoprev.c - average.twoprev.c), 2) +
    pow((vec->twoprev.a - average.twoprev.a), 2) +
    pow ((vec->twoprev.g - average. twoprev.g), 2) +
    pow((vec->twoprev.t - average.twoprev.t), 2) +
    pow((vec->prev.c - average.prev.c) *1.51 2) +
    pow((vec->prev.a - average.prev.a) *1.5, 2) +
    pow((vec->prev.g - average.prev.g) *1.5, 2) +
    pow((vec->prev.t - average.prev.t) *1.5, 2) +
    pow((vec->curr.c - average.curr.c) *2.0, 2) +
    pow((vec->curr.a - average.curr.a) *2.0, 2) +
    pow((vec->curr.g - average.curr.g) *2.0, 2) +
    pow((vec->curr.t - average.curr.t) *2.0, 2) +
    pow((vec->next.c - average.next.c) *1.5, 2) +
    pow((vec->next.a - average.next.a) *1.5, 2) +
    pow((vec->next.g - average.next.g) *1.5, 2) +
    pow((vec->next.t - average.next.t) *1.5, 2) +
    pow((vec->twonext.c - average.twonext.c), 2) +
    pow((vec->twonext.a - average.twonext.a), 2) +
    pow((vec->twonext.g - average.twonext.g) , 2) +
    pow((vec->twonext.t - average.twonext.t), 2)     ) *
    (pow(0.3*(vec->timetocall - average.timetocall), 2) + 1)
);
```

Prototype events for each of the sixteen doublets of DNA bases—CA,CC,CG,CT, . . . ,TA,TC,TT,TG are stored in the prototype file at step 1237. This file is mapped into the 20-dimensional signal-intensity subspace and 1-dimensional time-from-event-recognition subspace. Then all (20+1)-dimensional vectors at which a base is recognized are assembled according to which doublet is formed by the current and previous basecall. Vectors for each doublet are averaged arithmetically to form a prototype. The vector averages are output to memory.

Figure 15:
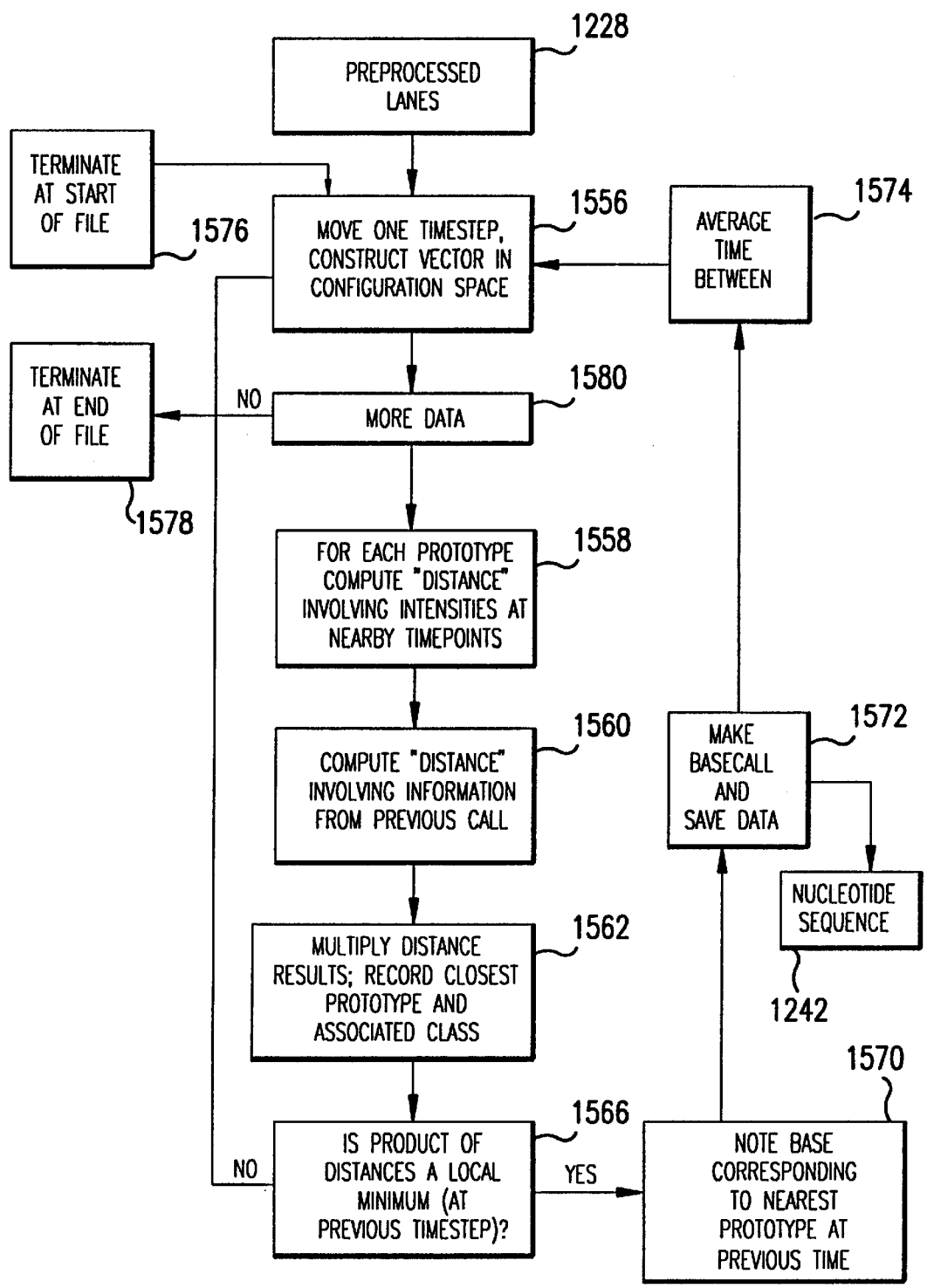
FIG. 15 shows the flow chart for the analysis basecalling step of FIG. 12.

A flow chart for the basecalling step is shown in FIG. 15. The basic processing loop is entered at step 1556; the next observation is input from memory; and a new vector is mapped in configuration space. Variables are initialized at step 1576, by looking forward a sufficient number of observations into the input data. Distances in the 20-dimensional signal-intensity subspace to all prototype events are computed at step 1558. The distance in the 1-dimensional time-from-event-recognition subspace is computed at step 1560. The two distances are multiplied at step 1562 to give the configuration space distance. The local distance minimum event recognition criterion is evaluated at step 1566. Illustratively, a local minimum is recognized when the path in configuration space has been nearest to a single prototype for at least three time points and the distance to that prototype at one time point is less than the distances at adjacent time points. If no event is recognized, the method returns to step 1556. If the criterion is met, that doublet event is recognized and saved at step 1570. Since the prior base recognized has been saved at step 1570, it and the currently recognized doublet are used to determine the current base at step 1572. This base and its recognition time is output at step 1242. Next (optionally), the average time between recognition events is updated by computing a moving average of the time between events. Adjustments from this average are made for known differences in electrophoretic mobility dependent on DNA sequence. Since the average time between basecalls depends on the nature of the separation gels, the voltage used, and other running conditions, it can be expected to vary from run to run. The average time between basecalls can also vary within a given run from start to finish.

Monte Carlo Proofreading step

The optional postprocessing consists of trimming known sequences at step 1238 then Monte Carlo proofreading at step 1240. Trimming known sequences includes removing known sub-sequences, usually vector DNA, from the processed data input from 1242.

Proofreading seeks to improve the overall match between the signal intensities and the recognized base events. The basecalling step looks locally at groups of observations representing two base recognition events seeking local minima. Proofreading tests the recognition globally by making proposed alterations (moves) and testing whether recognition accuracy is ultimately improved by the alterations. In this process, known restrictions on the DNA, such as it being a protein code, can be utilized. This is an important step for improving recognition accuracy. However, since it requires data from an entire analysis run, it cannot by used for sample selection and shunting.

Figure 16:
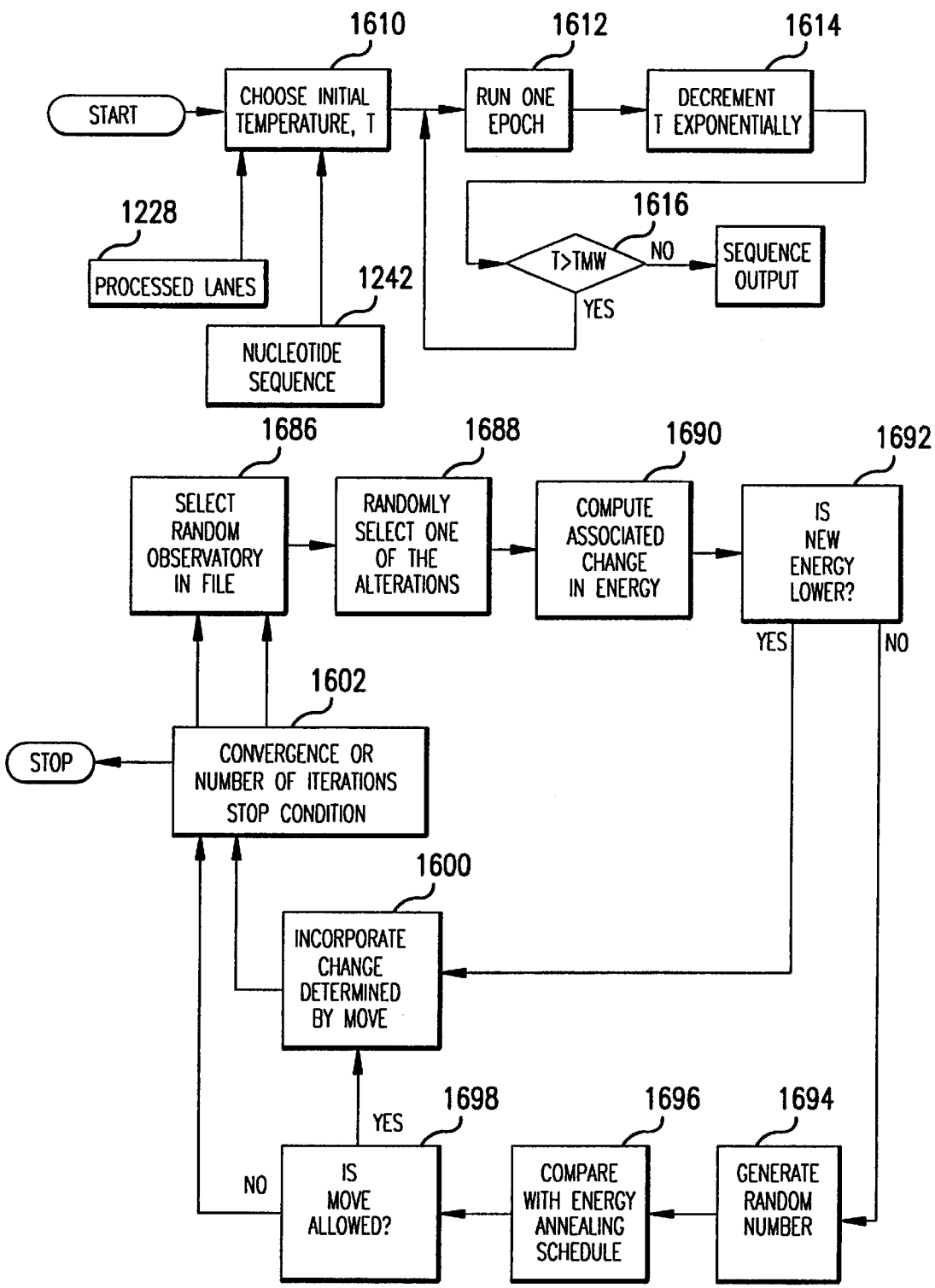
FIG. 16 shows the flow chart for the analysis proofreading step of FIG. 12.
Figure 172:
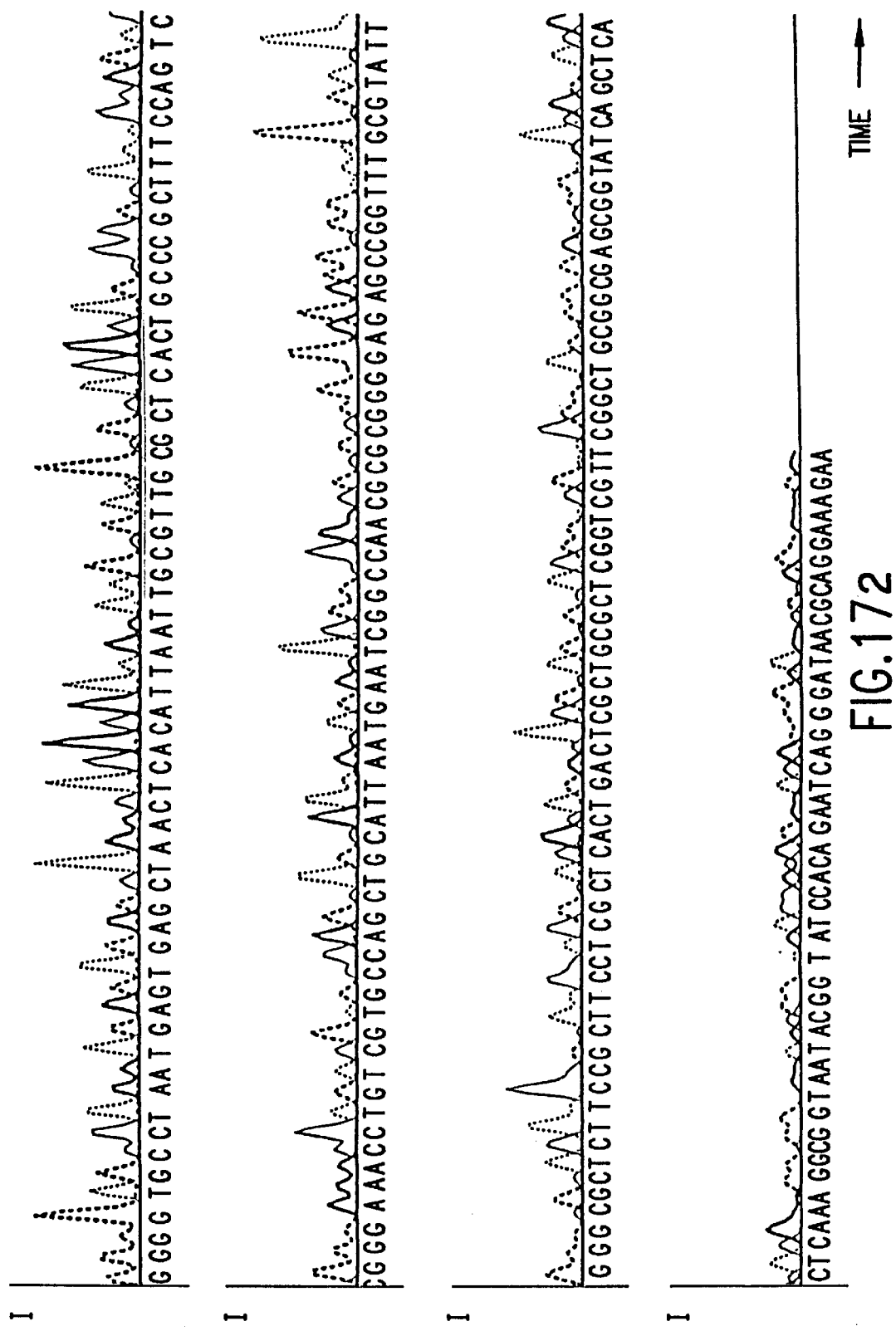

FIG. 16 provides flow charts of the Monte Carlo proofreading step. For conventional Monte Carlo techniques, refer to Press, et al., Numerical Recipes in C (1988), which is herein incorporated by reference. Monte Carlo proofreading requires three initial choices: a set of sequence alterations to try, an energy function to evaluate success of the alterations, and an annealing schedule to exercise overall control on the proofreading. The following are preferred choices. Choose for the set of alterations at an observation time: insert a new base recognition, delete a base recognition, move the nearest base recognition forward one observation time, or move the nearest base recognition backward one observation time. Other sets of alterations may incorporate specific knowledge about the DNA sample. For example, alterations should be limited to valid protein codons if the DNA is known to code for a protein. Choose for the energy function the sum over all base recognition events of the square of the distance in configuration space between the prototypes of the recognized base sequence and corresponding observation vectors. For the annealing schedule, choose a simulated temperature decay exponential in the number of epochs of the proofreading method, an epoch being a certain number of iterations of the alter-and-test loop. The simulated temperature probabilistically controls acceptance.

Proofreading begins at step 1610 with the choice of a temperature comparable to the value of the initial energy function. (Units are chosen so that the Boltzman constant is 1.0.) Next an epoch of proofreading is run at step 1612. The temperature is exponentially decremented at step 1614, by multiplication with a decay constant less than 1.0, and compared to a minimum. The decay constant determines the number of proofreading epochs to execute. If the temperature exceeds the minimum as tested at step 1616, the method loops back to step 1612. If not, the method ends at step 1616 and the base sequence with all permanently incorporated alterations is output to memory. The analysis method is complete.

The procedural steps in execution of one epoch of proofreading follow. The input data in memory is the base sequence output from the basecalling step 1242, as trimmed at step 1238, and the preprocessed signal traces 1228. The alter-and-test loop begins with selection of a random observation time from the sequencing run at step 1686 and a random sequence alteration from the chosen set of alterations at step 1688. A new energy is computed at step 1690 from the base sequence using the temporarily incorporated alteration and the input preprocessed signal traces. The new energy is tested at step 1692. If the new energy is lower than the previous energy, the alteration is permanently incorporated in the base sequence at step 1600. A convergence stop condition is tested at step 1602, which is preferably a certain number of alter-and-test iterations. Other stop conditions are possible, such as a certain energy decrement during the epoch. If the new energy is not lower, the move is allowed or disallowed probabilistically according to the Boltzmann criterion. A random number is generated at step 1694 to test the Boltzman probability of this move at step 1696. The Boltzman probability is determined by:

$$\text{Acceptance Probability} = \exp\left(-\frac{\text{energy change of move}}{T}\right) \quad (6)$$

where T is the current temperature of the epoch set at step 1614. If the move is allowed as tested at step 1698, it is permanently incorporated in the base sequence by step 1600. In either case the stop condition is again tested. If the stop condition is met, the epoch ends and overall stop condition at step 1616 is tested.

The following examples are illustrative of the application of the present invention.

EXAMPLE 1

Imaging Spectrograph and Analysis Method

A segment of double stranded DNA supplied as control with reagents from Applied Biosystems Inc. (Foster City, Calif.) (pGEM -3Zf(+) from the -21M13 forward primer) was analyzed.

Ultrafloat glass (with a green tinge) was used as the bottom plate. BK7 glass was used as the top plate. A 100 micron polyester spacer gasket separated the two pieces of glass. Bind silane, consisting of 1 milliliter of ethanol (J. T. Baker; Phillipsburg, N.J.), 5 microliters of gamma-methacryloxypropyltrimethoxysilane (Sigma Chemical Company; St. Louis, Mo.), and 50 microliters of 10 percent acetic acid (EM Science; Gibbstown, N.J.), was applied sparingly to each edge of glass which contacted the comb. The polycarbonate comb used had physical dimensions of 0.75 millimeter thickness, and teeth making wells in the gel spaced on 2.25 millimeter centers. Gel was 5 percent monomer 19:1 acrylamide:bisacrylamide Sequagel (National Diagnostics; Atlanta, Ga.) with 8.3M urea. The running buffer was 1×Tris-Borate-EDTA. The gel was allowed to polymerize for 3.5 hours, and was prerun for 0.5 hour. The sample was resuspended in 3–6 microliters of formamide/EDTA load solution. 0.5 microliters of sample were loaded into the gel.

The collection lens was a 250 mm f5.6 Zeiss medium format telephoto lens. Further description of the spectrograph is provided in the detailed description of the invention. Laser power of 82 milliwatts from an LS1000 argon ion laser (American Laser Corporation; Salt Lake City, Utah) was filtered to select the 515 nanometer wavelength using a laser line filter, resulting in about 35 milliwatts focused through the side of the gel. The electrophoresis path from the loading region to the detection region had a length of 23 or 24 centimeters. Exposure times were 2 seconds per frame. Detector read time was roughly 0.1 seconds. 4000 total frames were collected. Electrophoresis was conducted at 2500 Volts constant voltage applied across 28.5 centimeters using an EC 650 (E-C Apparatus Corporation; St. Petersburg, Fla.) power supply. This resulted in dissipation of 12.3 Watts in the gel. The circulated water was kept at 40 C. Samples were injected for 15–30 seconds.

The transmission imaging spectrograph recorded the fluorescence emitted by the labeled fragments. The seven lines of FIG. 17 show the trace of the preprocessed fluorescence intensities of the four dye labels as a function of time for one migration lane as output from the preprocessor. The letters underneath the time axis are the determined basecalls. Comparing to published data, from the center of the first line on there was perfect agreement, with the exception in the last line of one missing T and G (from a GGGG sequence). Correct functioning of the spectrograph and the analysis methods was demonstrated.

EXAMPLE 2

MicroFGE

Analyses were run with two conventional glass plate modules and the microFGE. The first conventional module has ultra-thin gel, with a 80 $\mu$m plate separation and a 23 cm migration path; the second is ultra-thin with a 80 $\mu$m separation and a 10 cm migration path. Both have 32 loading lanes formed with 2.25 mm center spacing. The microFGE has 80 channels, 80 micron deep on 1.125 mm center spacing and a 10 cm path.

The electrophoresis modules were loaded with 5% or 6% (19:1) polyacrylamide gels with 8.3 M urea. Well-forming combs formed the loading wells in the loading region 463. Bind silane (as above) assisted adhesion of gel to glass in the loading region. The gel was allowed to polymerize for 3 hours, at which point the well comb was removed leaving loading wells placed at the head of each migration lane. The running buffer was 1×TBE. The gel was then heated to a heat exchange temperature of 40° C.

Biopolymer fragment samples of a segment of M13 DNA were prepared, separated from the sequencing reaction medium, and resuspended in 3 $\mu$l of loading solution. For the microFGE 50–100 nl of the loading solution and for a conventional glass plate 400–500 nl were loaded into the loading wells. With a conventional glass plate, the 23 cm path from the loading region to the detection region resulted in separation of about 400 DNA bases in 2.5 hours with 2500 volts applied over 28.5 cm.

Figure 18A:
FIGS. 18A, 18B and 18C show recordings of illustrative output of the invention from three separation runs.
Figure 18B:
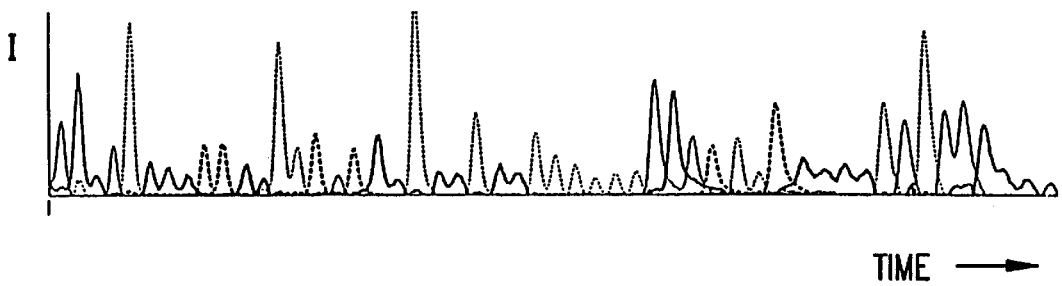
Figure 18C:
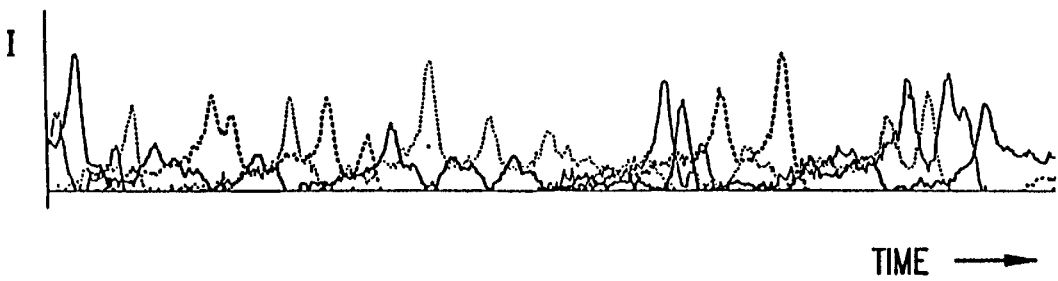

FIGS. 18A, 18B and 18C show the fluorescence traces from the transmission imaging spectrograph. In FIG. 18A the trace is from the glass plate module with ultra-thin plate spacing (90V/cm) and 23 cm path length. In FIG. 18B the trace is from the glass plate module with ultra-thin spacing at a 10 cm path length (100 V/cm). In FIG. 18C the trace shows results obtained with the 10 cm path of the microFGE (100 V/cm).

Figure 19A:
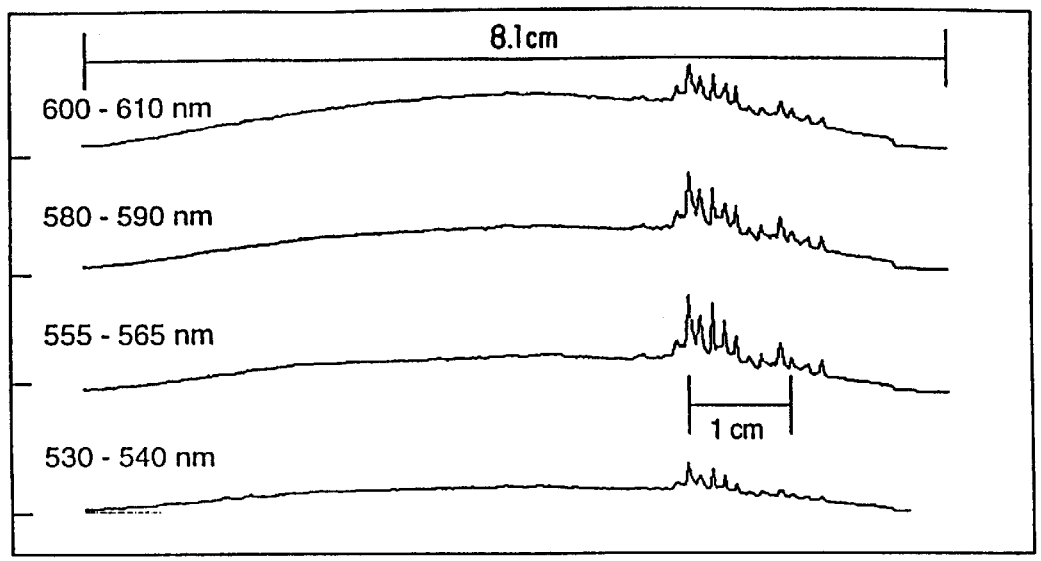
FIGS. 19A and 19B show recordings of the output of the spectrograph of FIG. 2A.
Figure 19B:
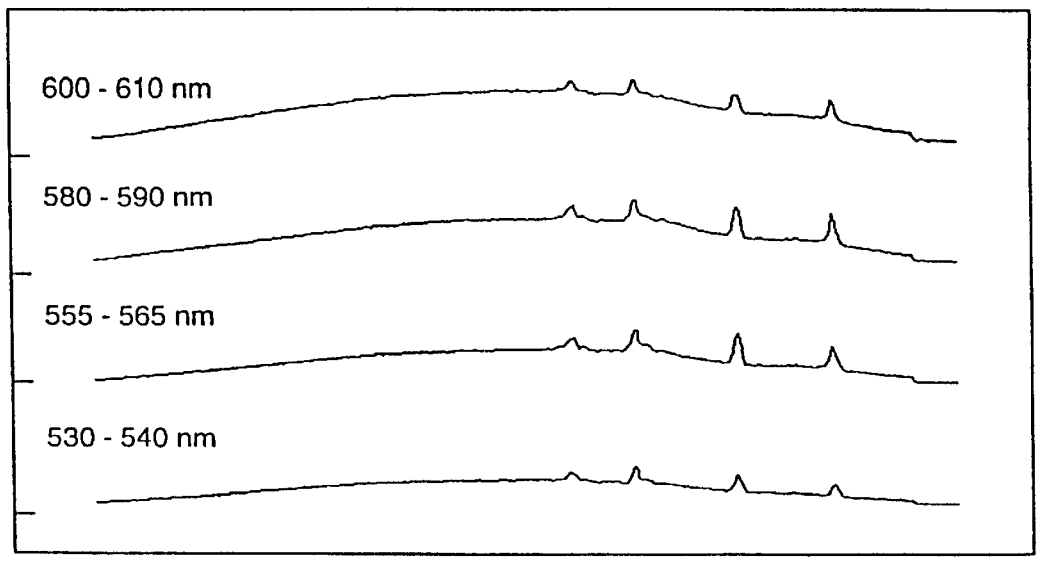

FIGS. 19A and 19B illustrate the output of the CCD array. They demonstrate the ability of the array to discriminate the signals from the different migration lanes and from different dyes.

Integrated functioning of the microFGE with the spectrograph were demonstrated. Further, the traces of FIGS. 18A, 18B, 18C, 19A and 19B provide evidence that: 1) a single well at the head of a microFGE lane can be loaded with a DNA fragment sample; 2) the DNA fragments are separated electrophoretically as they travel down a single lane in the microFGE; 3) the fragments exit the lane and move into the laser channel where they can be excited to fluorescence and imaged by the transmission imaging spectrograph; 4) the spatial broadening associated with exit from the lane is less than the spacing between the microFGE lanes; and 5) the dyes associated with the different nucleotides can be distinguished in time sufficient for base resolution.

As will be apparent to those skilled in the art, numerous variations may be made in the practice of our invention.

This invention is not limited to the use of any single sequencing chemistry; both chemical and enzymatic methods are enabled. By way of example, enzymatic methods can be used that do not rely on the use of chain terminator chemistry. Sequencing in an integrated device may be enabled by sequence ladder generation techniques other than Sanger methods. A coupled procedure can be used that will rely on the generation of PCR-amplified products and subsequent direct generation of ladders by exonuclease digestion. This is made possible by the incorporation of blocking base analogs for A, C, G, and T that allow for the PCR extension to proceed to completion in each cycle, but that cause 5' to 3' activity of single strand exonucleases (e.g. Exo I; New England Biolabs; Beverly, Mass.) to be blocked. After four separate PCR reactions, each with a single modified blocking base, the products can be digested with an exonuclease, thereby producing a set of nested fragments terminating at each point of incorporation of the blocking base analog. Suitable use of dye labeled primers allows for the identification of the blocking base which terminates the fragment. These blocking bases are made by incorporating substitutions into the chemical structure of the DNA bases which allow the base to be incorporated by enzymatic action in a growing DNA strand, and also allow such strand to be a template for growth of a complementary strand (DOE Human Genome Project Report, Spring 1995). Use of non-chain-terminating fluorescent labels attached to the blocking base analogs would enable reactions performed in a single vessel. Biotin immobilization can be used on one primer to allow strand separation and separate analysis of the fragment ladders generated from each complementary strand.

Chemistry techniques producing sequence fragments from both complementary strands of DNA also are enabled by our invention. Chemistry techniques for generating ladders of sequence fragments have previously been used to generate fragments from, and therefore information about a single strand at a time. With the full spectral capability of the instrument, and with the analysis capability of the software, it is possible to resolve sequence information directly generated from both strands simultaneously, thereby increasing the accuracy, robustness and reliability of analysis of a biopolymer sample. In one example, two different primers are used for the two ends of the two strands of DNA. Standard Sanger fragment ladders are generated corresponding to both strands along the DNA in a single reaction, with opposite directions (strands) having unique dye labeled primers. The dyes are chosen to be spectrally resolvable. A strategy incorporating four dyes readily allows both strands of a fragment to be sequenced in two lanes, each lane corresponding to sequence information on two bases (e.g. C and T) for each of the two strands. Advantageously, a strategy incorporating eight spectrally resolvable dyes allows simultaneous independent analysis of both sequencing ladders in a single lane. Binary coding strategy can be used to decrease the number of dyes required to perform the same simultaneous independent analysis of a biopolymer fragment.

A variety of solid-phase supports can be used to bring either reactants, template or product into or out of the sample loading wells or microfabricated reaction vessels. Products and templates can be coupled to the support either covalently or non-covalently. Examples of non-covalent attachment are (streptavidin-biotin), and (antibody-small epitope). Hybridization between complementary strands of DNA is an alternative non-covalent attachment means.

Covalent attachments made via disulfide bonds are also useful; release of the attached species is accomplished by a change in reduction potential resulting in the break of the disulfide bond. Techniques eliminating the need for chemical separation steps in the reaction process are ideally matched to the invention, and are enabled, for example, by solid-phase magnetic separations. Specifically, minute magnetic beads (Dynal Corporation) are used in standard biochemical protocols for material transport, and are a suitable substitute for the fixed teeth of a comb used for solid-phase loading. Streptavidin coated magnetic beads can be processed in the same manner as the combs. Minute magnetic bead allow for quantitation of sample transport and are suitable for loading means based on mechanisms for moving magnetic particles (C. H. Ahn and M. G. Allen, "A Fully Integrated Micromachined Magnetic Particle Manipulator and Separator"). The transport of reaction products on magnetic beads also allows for the concurrent separation of reaction products and unreacted reagent mixtures.

Numerous variations may also be practiced in the signal processing used to identify the nucleotides and the same techniques may be used in other signal matching applications. For example, the comparisons may be made using data representative of triples of nucleotides instead of pairs of nucleotides; and other matching strategies may be used.

What is claimed is:

1. A method for determining the DNA sequences of a plurality of DNA samples, the method using spectral signals obtained by spectrographic detection of electrophoretically separated labeled DNA fragments in a plurality of migration lanes, the fragments in each of said samples being produced from one or more DNA templates primed with one or more sequencing primers and being labeled with dyes having distinctive spectral properties, the method comprising the sequential steps of:

(1) binning spectrographic signal intensities acquired at each of a plurality of observation times from each of said plurality of migration lanes into a spatial signal set to obtain a plurality of spatial signal sets for each said observation time and into spectral signal sets where each spatial signal set represents the distinctive spectral properties of one of a plurality of said dyes, wherein each spatial signal set and each spectral signal set contain signal intensities from one migration lane, wherein each migration lane contains the fragments from one DNA sample, said plurality of dyes being used to label fragments in said sample;

(2) repeating step (1) for spectrographic signal intensities acquired at each observation time to obtain time behaviors of said spectral signals;

(3) comparing for each spatial signal set the time behaviors of said spectral signals in each of said plurality of spatial signal sets with time behaviors of a set of prototype signals corresponding to a set of prototypes;

(4) selecting prototypes from said set of prototype signals that most closely match said spectral signals; and (5) outputting the selected prototypes, thereby determining the sequences of said plurality of DNA samples;

wherein said spectrographic signal intensities are input from a transmission imaging spectrograph which detected signal intensities measured simultaneously for said plurality of migration lanes and for said plurality of spectral values at each of said plurality of observation times; and wherein each of said migration lanes contains one or more sets of said labeled DNA fragments, said labeled DNA fragments in each said set being characterized by being produced from a certain DNA template primed with a certain sequencing primer and having a certain nucleotide at the 3' end, wherein each set of said labeled DNA fragments in each sample is labeled with one or more dyes distinguishable by distinctive spectral properties from the dyes labeling the other sets of fragments in said sample.

2. The method of claim 1, wherein the time behaviors of the set of prototype signals are obtained from the analysis of known DNA sequences.

3. The method of claim 2 wherein the selected prototypes are pairs of sequential DNA fragments.

4. The method of claim 1 wherein the step of selecting comprises determining a distance between the time behaviors of the spectral signals and the time behaviors of the prototypes and selecting as representative that prototype providing the smallest distance.

5. The method of claim 4 wherein the distance is the sum of the squares of the differences in signal values between the spectral signals and the prototype signals.

6. The method of claim 4 wherein the distance is the product of (x), the sum of the squares of the differences in signal values between the spectral signals and the prototype signals, and (y), a distance representing the difference between the expected time between observation times of closest match, and the actual time between observation times of closest match.

7. The method of claim 6 in which the distance (y) is a function of the square of the difference between the expected time between observation times of closest match and the actual time between observation times of closest match.

8. The method of claim 7 further comprising the steps of:

(1) trimming from each of the output sequences of the DNA samples a portion of said sequence said portion being known to be present in the DNA sequencing template;

(2) proofreading each of the trimmed DNA sequences, the step of proofreading comprising repetitively making at a random point in the trimmed DNA sequence a random sequence alteration and evaluating sequence improvement until no further substantial sequence improvement occurs; and (3) outputting each improved sequence.

9. The method of claim 8 wherein evaluating sequence improvement is done by comparing an energy function of a distance between the signals of original DNA sequence and the spectral signals with an energy function of said distance between the signals of said trimmed DNA sequence having a random sequence alteration and the spectral signals.

10. The method of claim 1, wherein each one of said plurality of migration lanes contains the fragments produced from one DNA sequencing template.

11. The method of claim 1 or 10, wherein said fragments are generated by a Sanger sequencing reaction.

12. The method of claim 11, wherein said Sanger sequencing reaction uses more than one species of dideoxynucleotide, each species of dideoxynucleotide being labeled with a different dye having a distinctive spectral property.

13. The method of claim 1 or 10, wherein said fragments are generated by PCR amplification and subsequent exonuclease digestion.

14. The method of claim 13, wherein said fragments are generated using more than one primer, each primer being labeled with a different dye having a distinctive spectral property.

15. The method of claim 13, wherein said fragments are generated using more than one blocking base analog, each blocking base analog being labeled with a different dye having a distinct emission spectrum.

* * * * *